US012760319B2

(12) United States Patent
Muchero et al.

(10) Patent No.: US 12,760,319 B2
(45) Date of Patent: Oct. 13, 2026

(54) PLANTS WITH ENHANCED PHOTOSYNTHETIC EFFICIENCY AND BIOMASS YIELD

(71) Applicants: UT-Battelle, LLC, Oak Ridge, TN (US); University of Tennessee Research Foundation, Knoxville, TN (US); The Board of Trustees of the University of Illinois, Urbana, IL (US)

(72) Inventors: Wellington Muchero, Oak Ridge, TN (US); Jin-Gui Chen, Oak Ridge, TN (US); Biruk Ayenew Feyissa, Norwich (CA); Gerald A. Tuskan, Oak Ridge, TN (US); Timothy B. Yates, Fountain Valley, CA (US); Elsa De Becker, Urbana, IL (US); Steven J. Burgess, Urbana, IL (US); Stephen P. Long, Champaign, IL (US); Mengjun Shu, Knoxville, TN (US)

(73) Assignees: 'UT-Battelle, LLC, Oak Ridge, TN (US); University of Tennessee Research Foundation, Knoxville, TN (US); The Board of Trustees of the University of Illinois, Urbana, IL (US)

( * ) Notice: Subject to any disclaimer, the term of this patent is extended or adjusted under 35 U.S.C. 154(b) by 215 days.

(21) Appl. No.: 18/477,640

(22) Filed: Sep. 29, 2023

(65) Prior Publication Data

US 2024/0401071 A1 Dec. 5, 2024

Related U.S. Application Data

(60) Provisional application No. 63/469,847, filed on May 31, 2023.

(51) Int. Cl.

*C12N 15/82* (2006.01)
*C12N 9/88* (2006.01)

(52) U.S. Cl.

CPC ........... *C12N 15/8269* (2013.01); *C12N 9/88* (2013.01); *C12Y 401/01039* (2013.01)

(58) Field of Classification Search

CPC .................. C12N 15/8269; C12N 9/88; C12Y 401/01039

See application file for complete search history.

(56) References Cited

U.S. PATENT DOCUMENTS 8,343,764 B2 1/2013 Abad et al.
2013/0273613 A1 10/2013 Devroe et al.

(Continued)

OTHER PUBLICATIONS

Wang, T., Li, L., Cheng, G., Shu, X., Wang, N., Zhang, F., . . . & Wang, Z. (2021). Physiological and molecular analysis reveals the differences of photosynthesis between colored and green leaf poplars. International Journal of Molecular Sciences, 22(16), 8982. (Year: 2021).*

(Continued)

*Primary Examiner* — Amjad Abraham
*Assistant Examiner* — Dequantarius Javon Speed
(74) *Attorney, Agent, or Firm* — Scully, Scott, Murphy & Presser, P.C.

(57) ABSTRACT

The present disclosure is directed to genetically modified plants, plant cells, or plant tissues wherein the genetic modification comprises expression of an exogenous nucleic acid comprising a ribulose bisphosphate carboxylase/oxygenase large subunit-related (PRL-1) gene or homolog thereof, in the plant, plant cell, or plant tissue; and wherein the expression of the exogenous nucleic acid comprising the PRL-1 gene or homolog thereof results in enhanced photosynthetic efficiency and/or plant biomass of the plant, plant cell, or plant tissue as compared to a wild-type plant, plant cell or plant tissue without the genetic modification. Another aspect of the current disclosure is directed to methods of enhancing photosynthetic efficiency and biomass yield in a (Continued)

plant, plant cell, or plant tissue, the methods comprising expressing an exogenous nucleic acid comprising a PRL-1 gene or homolog thereof.

16 Claims, 24 Drawing Sheets
(7 of 24 Drawing Sheet(s) Filed in Color)

Specification includes a Sequence Listing.

(56) References Cited

U.S. PATENT DOCUMENTS

2019/0112617 A1* 4/2019 Yohn .................. C12N 15/8261
2021/0072228 A1 3/2021 Muchero et al.

OTHER PUBLICATIONS

Tabita, F. R., Hanson, T. E., Li, H., Satagopan, S., Singh, J., & Chan, S. (2007). Function, structure, and evolution of the RubisCO-like proteins and their RubisCO homologs. Microbiology and Molecular Biology Reviews, 71(4), 576-599. (Year: 2007).*
Wang, Zhanchao, Quangang Liu, Hanzeng Wang, Haizhen Zhang, Xuemei Xu, Chenghao Li, and Chuanping Yang. "Comprehensive analysis of trihelix genes and their expression under biotic and abiotic stresses in Populus trichocarpa." Scientific Reports 6, No. 1 (2016): 36274. (Year: 2016).*
Tharasirivat, Vetaka, and Saowarath Jantaro. "Increased biomass and polyhydroxybutyrate production by *Synechocystis* sp. PCC 6803 overexpressing RuBisCO genes." International journal of molecular sciences 24.7 (Mar. 2023): 6415. (Year: 2023).*
(Y) Martin-Avila, E., Lim, Y. L., Birch, R., Dirk, L. M., Buck, S., Rhodes, T., . . . & Whitney, S. M. (2020). Modifying plant photosynthesis and growth via simultaneous chloroplast transformation of Rubisco large and small subunits. Plant Cell, 32(9), 2898-2916. (Year: 2020).*
(Z) Qu, Y., Sakoda, K., Fukayama, H., Kondo, E., Suzuki, Y., Makino, A., . . . & Yamori, W. (2021). Overexpression of both Rubisco and Rubisco activase rescues rice photosynthesis and biomass under heat stress. Plant, Cell & Environment, 44(7), 2308-2320. (Year: 2021).*
Anderson, L. E., & Carol, A. A. (2004). Enzyme co-localization with Rubisco in pea leaf chloroplasts. Photosynthesis research, 82(1), 49-58. (Year: 2004).*
Lazar, E., Vicenzi, E., Van Obberghen-Schilling, E., Wolff, B., Dalton, S., Watanabe, S., & Sporn, M. B. (1989). Transforming growth factor a: An aromatic side chain at position 38 is essential for biological activity. Molecular and cellular biology, 9(2), 860-864. (Year: 1989).*
Nonaka, T., Kametani, F., Arai, T., Akiyama, H., & Hasegawa, M. (2009). Truncation and pathogenic mutations facilitate the formation of intracellular aggregates of TDP-43. Human molecular genetics, 18(18), 3353-3364. (Year: 2009).*
Hanna Horak, Back to Where It Came From: Chloroplast Expression of Both Rubisco Subunits Helps Functional Enzyme Analysis, The Plant Cell, vol. 32, Issue 9, Sep. 2020, pp. 2677-2678, https://doi.org/10.1105/tpc.20.00544 (Year: 2020).*
Zhu X-G et al., "The Slow Reversibility of Photosystem II Thermal Energy Dissipation on Transfer from High to Low Light May Cause Large Losses in Carbon Gain by Crop Canopies: a Theoretical Analysis", *Journal of Experimental Botany* 55(400):1167-1175 (May 2004).
GenBank Accession No. AC216678 (10 pages) (Jan. 17, 2008) (cited in ISR & Written Opinion).
GenBank Accession No. AB012779.1 (2 pages) (Jul. 26, 2016) (cited in ISR & Written Opinion).
UniProt Accession No. Q95B16_9ROSA (2 pages) (Dec. 1, 2001) (cited in ISR & Written Opinion).
International Search Report and Written Opinion dated Apr. 12, 2024 received in International Application No. PCT/US2023/75482.
Andersson I., "Catalysis and Regulation in Rubisco", Journal of Experimental Botany 59(7):1555-1568 (2008).
Ainsworth E.A. et al., "30-Years of Free-Air Carbon Dioxide Enrichment (FACE): What Have We Learned About Future Crop Productivity and its Potential for Adaptation?", Glob Change Biol. 27(1):27-49 (Sep. 2020).
Arendsee Z.W. et al., "Coming of Age: Orphan Genes in Plants", Trends in Plant Science 19(11):698-708 (Nov. 2014).
Aubin E. et al., "Horizontal Gene Transfers in Plants", Life 11(8):857 (2021).
Babiychuk E. et al., "Plastid Gene Expression and Plant Development Require a Plastidic Protein of the Mitochondrial Transcription Termination Factor Family", PNAS 108(16):6674-6679 (Apr. 19, 2011).
Bar-On Y.M. et al., "The Global Mass and Average Rate of Rubisco", PNAS 116(10):4738-4743 (Mar. 5, 2019).
Batth T.S. et al., "Protein Aggregation Capture on Microparticles Enables Multipurpose Proteomics Sample Preparation", Mol Cell Proteomics 18(5):1027-1035 (2019).
Carmo-Silva A.E. et al., "The Regulatory Properties of Rubisco Activase Differ Among Species and Affect Photosynthetic Induction During Light Transitions", Plant Physiology 161:1645-1655 (Apr. 2013).
Cassman K.G. et al., "Meeting Cereal Demand While Protecting Natural Resources and Improving Environmental Quality", Annual Review of Environment and Resources 28:315-358 (2003).
Cen Y-P et al., "The Regulation of Rubisco Activity in Response to Variation in Temperature and Atmospheric CO2 Partial Pressure in Sweet Potato", Plant Physiology 139:979-990 (Oct. 2005).
Chhetri H.B. et al., "Multitrait Genome-Wide Association Analysis of Populus Trichocarpa Identifies Key Polymorphisms Controlling Morphological and Physiological Traits", New Phytologist 223:293-309 (2019).
Clough S.J. et al., "Floral Dip: A Simplified Method for Agrobacterim-Mediated Transformation of *Arabidopsis thaliana*", The Plant Journal 16(6):735-743 (1998).
Dall'Osto L. et al., "On the Origin of a Slowly Reversible Fluorescence Decay Component in the *Arabidopsis* npq4 Mutant", Philosophical Transactions of the Royal Society B 369(1640):20130221 (2014).
Desouza A.P. et al., "Soybean Photosynthesis and Crop Yield are Improved by Accelerating Recovery from Photoprotection", Science 377(6608):851-854 (Aug. 19, 2022).
Duursma R.A., "Plantecophys—An R Package for Analysing and Modelling Leaf Gas Exchange Data", PLoS ONE 10(11):e0143346 (2015).
Evans L.M. et al., "Population Genomics of Populus Trichocarpa Identifies Signatures of Selection and Adaptive Trait Associations", Nature Genetics 46(10):1089-1096 (Oct. 2014).
Feyissa B.A. et al., "Transcriptome-IPMS Analysis Reveals a Tissue-Dependent miR156/SPL13 Regulatory Mechanism in Alfalfa Drought Tolerance", BMC Genomics 21:721 (2020).
Garcia-Molina A. et al., "Accelerated Relaxation of Photoprotection Impairs Biomass Accumulation in *Arabidopsis*", Nature Plants 6(1):9-12 (Jan. 2020).
Grassini P. et al., "Distinguishing Between Yield Advances and Yield Plateaus in Historical Crop Production Trends", Nature Communications 4(2918) (2013).
Gotarkar D. et al., "High-Throughput Analysis of Non-Photochemical Quenching in Crops Using Pulse Amplitude Modulated Chlorophyll Fluorometry", JoVE Journal of Visualized Experiments 185(e63485):1-14 (Jul. 2022).
Hazkani-Covo E. et al., "Quantifying the Number of Independent Organelle DNA Insertions in Genome Evolution and Human Health", Genome Biol. Evol. 9(5):1190-1203 (2017).
Huang C.Y. et al., "Direct Measurement of the Transfer Rate of Chloroplast DNA into the Nucleus", Nature 422(6927):72-76 (Mar. 6, 2003).

(56) References Cited

OTHER PUBLICATIONS

Kall L. et al., "Semi-Supervised Learning for Peptide Identification from Shotgun Proteomics Datasets", Nature Methods 4(11):923-925 (Nov. 2007).
Kromdijk J. et al., "Improving Photosynthesis and Crop Productivity by Accelerating Recovery from Photoprotection", Science 354(6314):857-861 (Nov. 18, 2016).
Lehretz G.G. et al., "High Non-Photochemical Quenching of VPZ Transgenic Potato Plants Limits CO2 Assimilation Under High Light Conditions and Reduces Tuber Yield Under Fluctuating Light", Journal of Integrative Plant Biology 64(9):1821-1832 (Sep. 2022).
Letran A. et al., "Measurement of IgE to Pollen Allergen Components is Helpful in Selecting Patients for Immunotherapy", Ann Allergy Asthma Immunol 111:295-297 (2013).
Long S.P. et al., "Into the Shadows and Back into Sunlight: Photosynthesis in Fluctuating Light", Annu Rev Plant Biol. 73: 617-648 (May 2022).
Long S.P. et al., "Food for Thought: Lower-Than-Expected Crop Yield Stimulation With Rising CO2 Concentrations", Science 312:1918-1921 (Jun. 30, 2006).
Lopez-Maury L. et al., "Tuning Gene Expression to Changing Environments: from Rapid Responses to Evolutionary Adaptation", Nature Reviews—Genetics 9(8):583-593 (Aug. 2008).
Martin W.F. et al., "Endosymbiotic Theories for Eukaryote Origin", Philosophical Transactions of the Royal Society B 370:20140330 (2015).
Muchero W. et al., "Association Mapping, Transcriptomics, and Transient Expression Identify Candidate Genes Mediating Plant-Pathogen Interactions in a Tree", PNAS 115(45):11573-11578 (Nov. 6, 2018).
Muchero W. et al., "High-Resolution Genetic Mapping of Allelic Variants Associated With Cell Wall Chemistry in Populus", BMC Genomics 16(24): 1-14 (2015).
Parry M.A.J. et al., "Rubisco Activity and Regulation as Targets for Crop Improvement", Journal of Experimental Botany 64(3):717-30 (2013).
Pingali P.L., "Green Revolution: Impacts, Limits, and the Path Ahead", PNAS 109(31):12302-12308 (Jul. 31, 2012).
Richly E. et al., "NUPTs in Sequenced Eukaryotes and Their Genomic Organization in Relation to NUMTs", Molecular Biology and Evolution 21(10):1972-1980 (2004).
Seguel A. et al., "Prohibitin3 Forms Complexes With Isochorismate Synthase1 to Regulate Stress-Induced Salicylic Acid Biosynthesis in *Arabidopsis*", Plant Physiology 176:2515-2531 (Mar. 2018).
Taylor S.H. et al., "Faster Than Expected Rubisco Deactivation in Shade Reduces Cowpea Photosynthetic Potential in Variable Light Conditions", Nature Plants 8:118-124 (Feb. 2022).
Taylor S.H. et al., "Slow Induction of Photosynthesis on Shade to Sun Transitions in Wheat May Cost at Least 21% of Productivity", Philosophical Transactions of the Royal Society B 372(1730):20160543 (2017).
Theeuwen T.P.J.M. et al., "Genetics as a Key to Improving Crop Photosynthesis", Journal of Experimental Botany 73(10):3122-3137 (2022).
Thormahlen I. et al., "Thioredoxins Play a Crucial Role in Dynamic Acclimation of Photosynthesis in Fluctuating Light", Molecular Plant 10(1):168-182 (Jan. 2017).
Thorsness P E et al., "Escape of DNA from Mitochondria to the Nucleus in *Saccharomyces cerevisiae*", Nature 346(6282):376-379 (Jul. 26, 1990).
Vitale A. et al., "The Role of the Endoplasmic Reticulum in Protein Synthesis, Modification and Intracellular Transport", Journal of Experimental Botany 44(266):1417-1444 (Sep. 1993).
Walker B.J. et al., "The Costs of Photorespiration to Food Production Now and in the Future", The Annual Review of Plant Biology 67:107-129 (2016).
Wang Y. et al., "Photosynthesis in the Fleeting Shadows: an Overlooked Opportunity for Increasing Crop Productivity?", The Plant Journal 101:874-884 (2020).
Wei W. et al., "Nuclear-Embedded Mitochondrial DNA Sequences in 66,083 Human Genomes", Nature 611:105-114 (Nov. 3, 2022).
Woodson J.D. et al., "Coordination of Gene Expression Between Organellar and Nuclear Genomes", Nat Rev Genet. 9(5):383-395 (May 2008).
Xie M. et al., "A 5-Enolpyruvylshikimate 3-Phosphate Synthase Functions as a Transcriptional Repressor in Populus", The Plant Cell 30(7):1645-1660 (Jul. 2018).
Yates T.B. et al., "The Ancient Salicoid Genome Duplication Event: A Platform for Reconstruction of De Novo Gene Evolution in Populus Trichocarpa", Genome Biol. Evol. 13(9):evab198 (2021).
Zhang N. et al., "Mechanism of Light Regulation of Rubisco: A Specific Role for the Larger Rubisco Activase Isoform Involving Reductive Activation by Thioredoxin-f", Proc. Natl. Acad. Sci. USA 96:9438-9443 (Aug. 1999).
Zhou X. et al., "Genome-Wide Efficient Mixed Model Analysis for Association Studies", Nat Genet. 44(7):821-824 (2012).
Wang T. et al., "Physiological and Molecular Analysis Reveals the Differences of Photosynthesis Between Colored and Green Leaf Poplars", International Journal of Molecular Sciences 22:1-17 (2021).
Invitation to Pay Additional Fees dated Jan. 25, 2024 received in International Application No. PCT/US2023/075482.

* cited by examiner

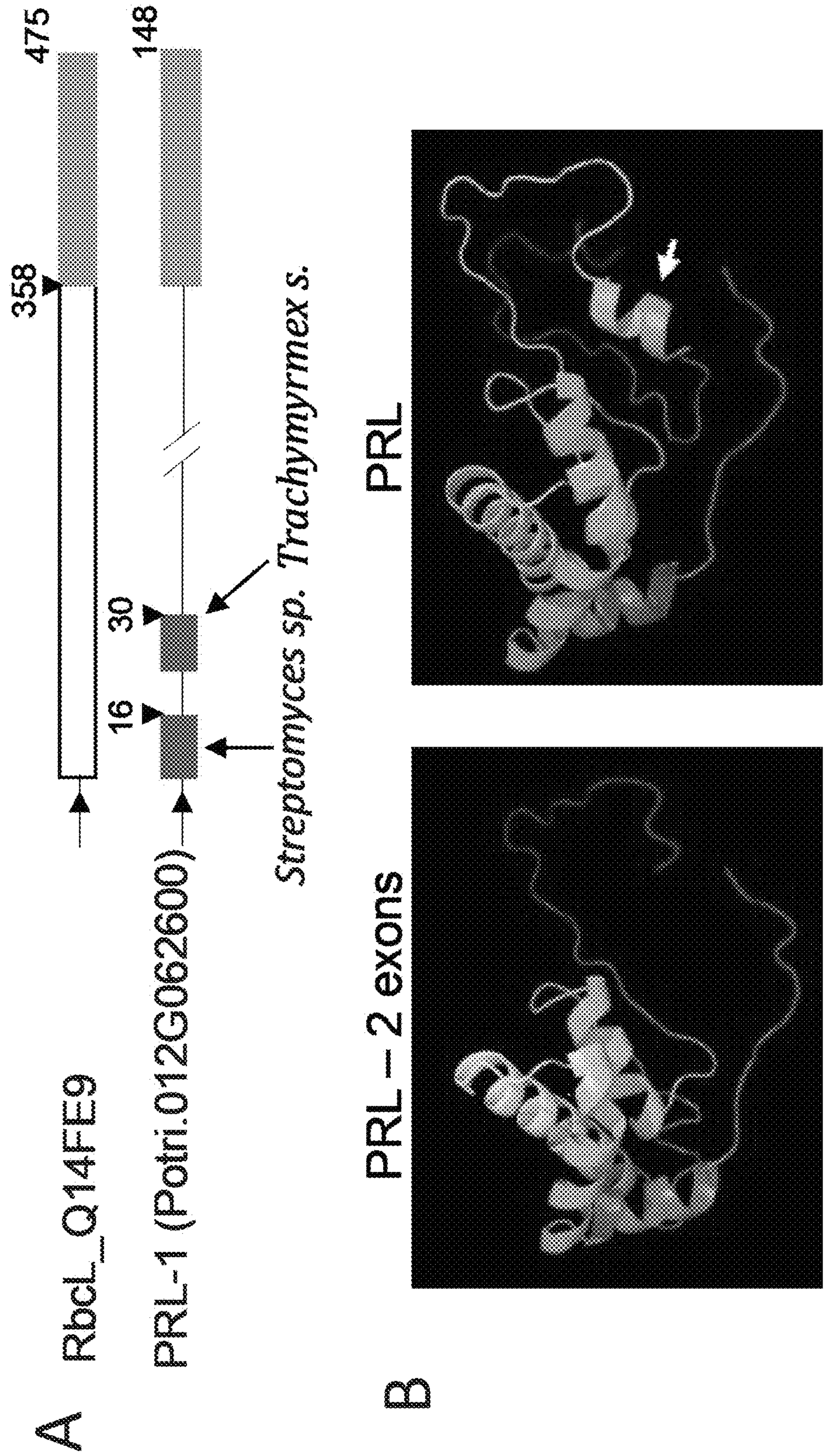
FIG. 1A-B

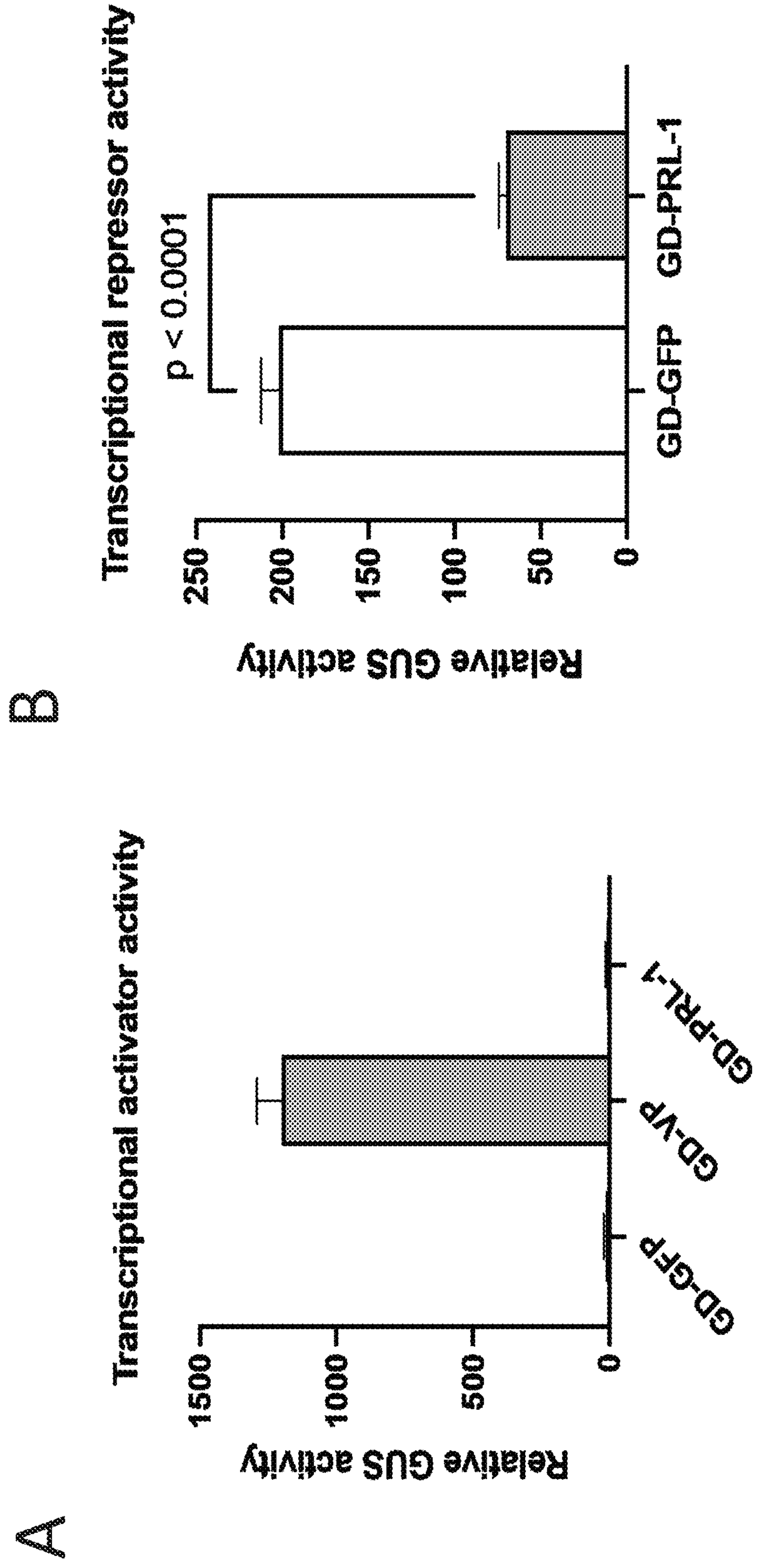
FIG. 3A-B

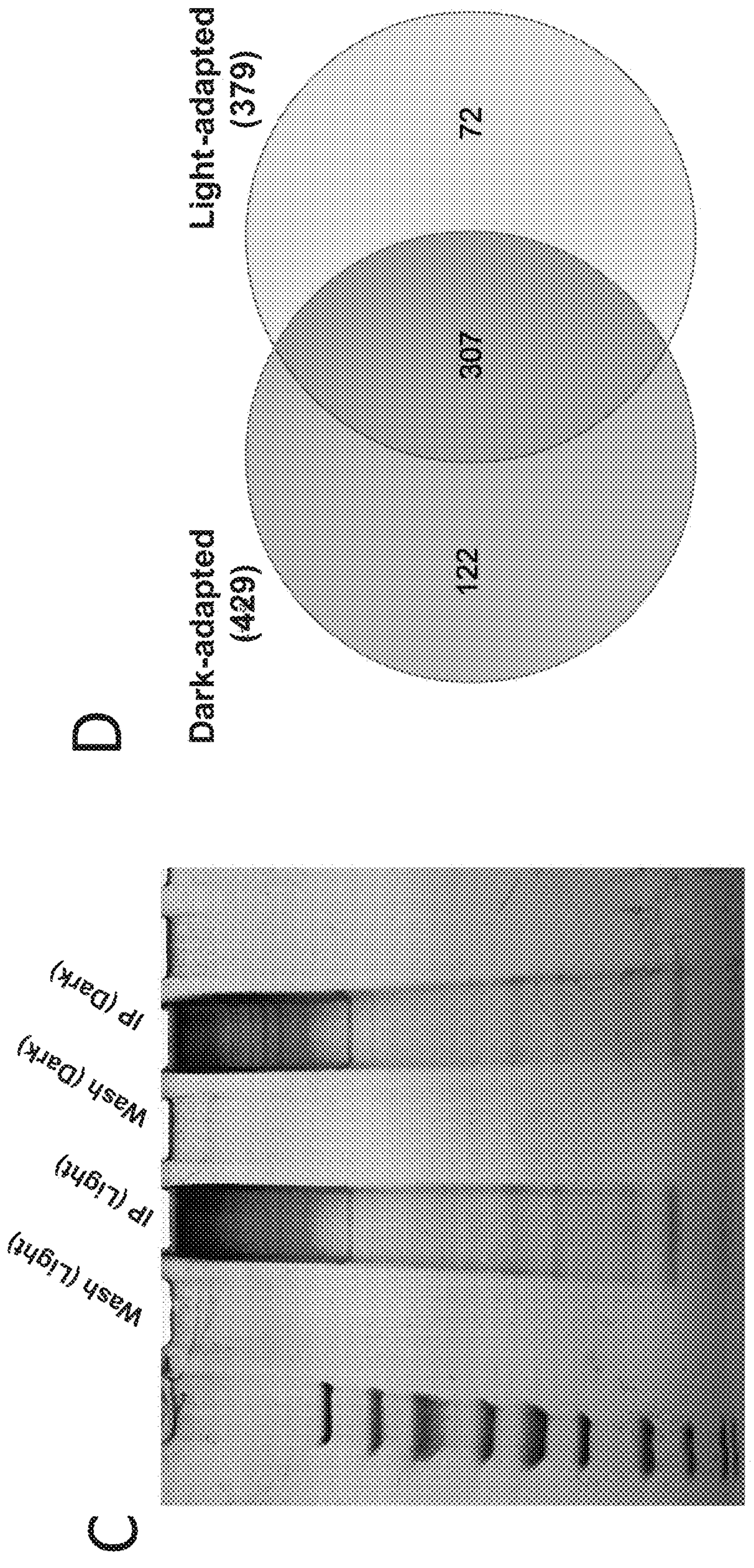
FIG. 3C-D

E

A

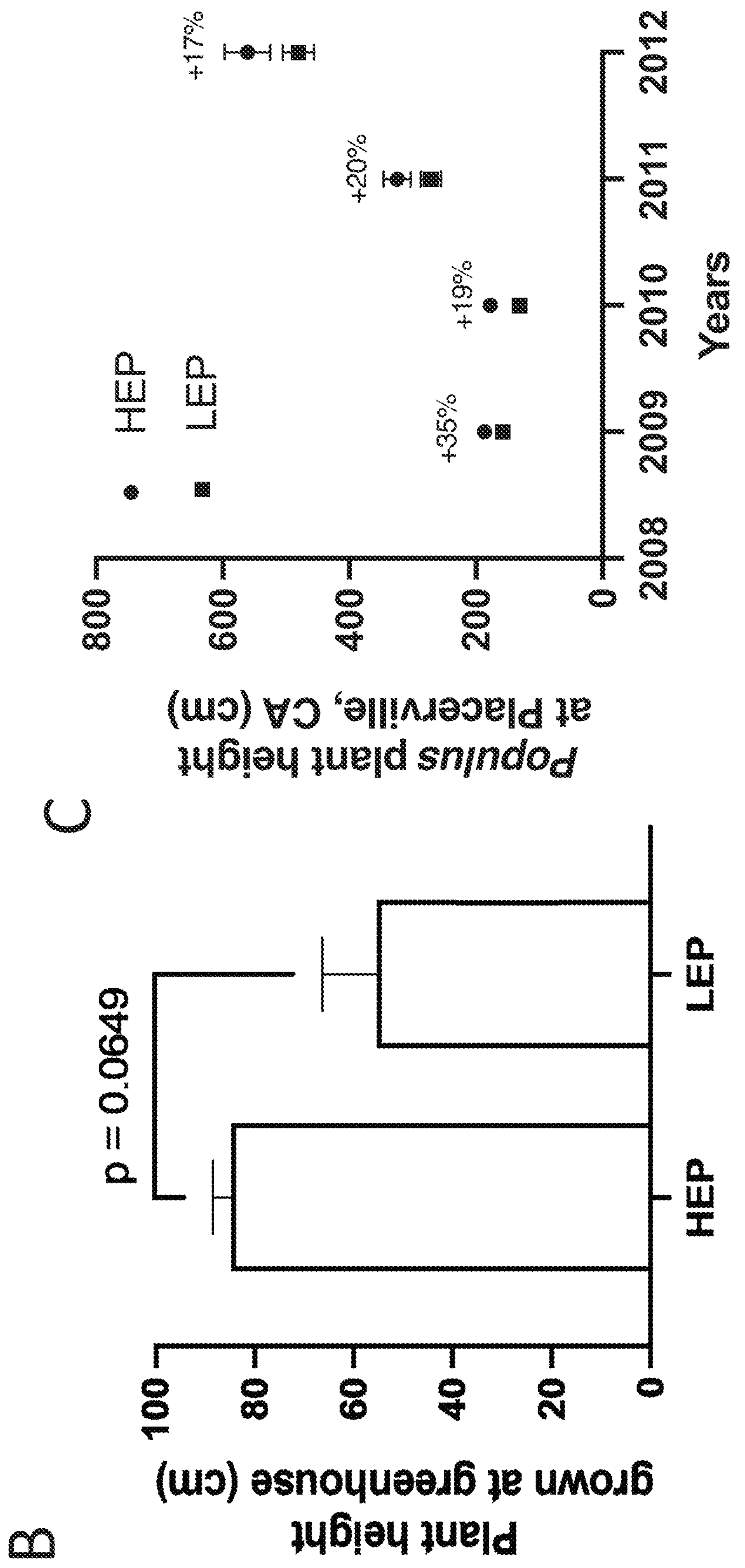
FIG. 5B-C

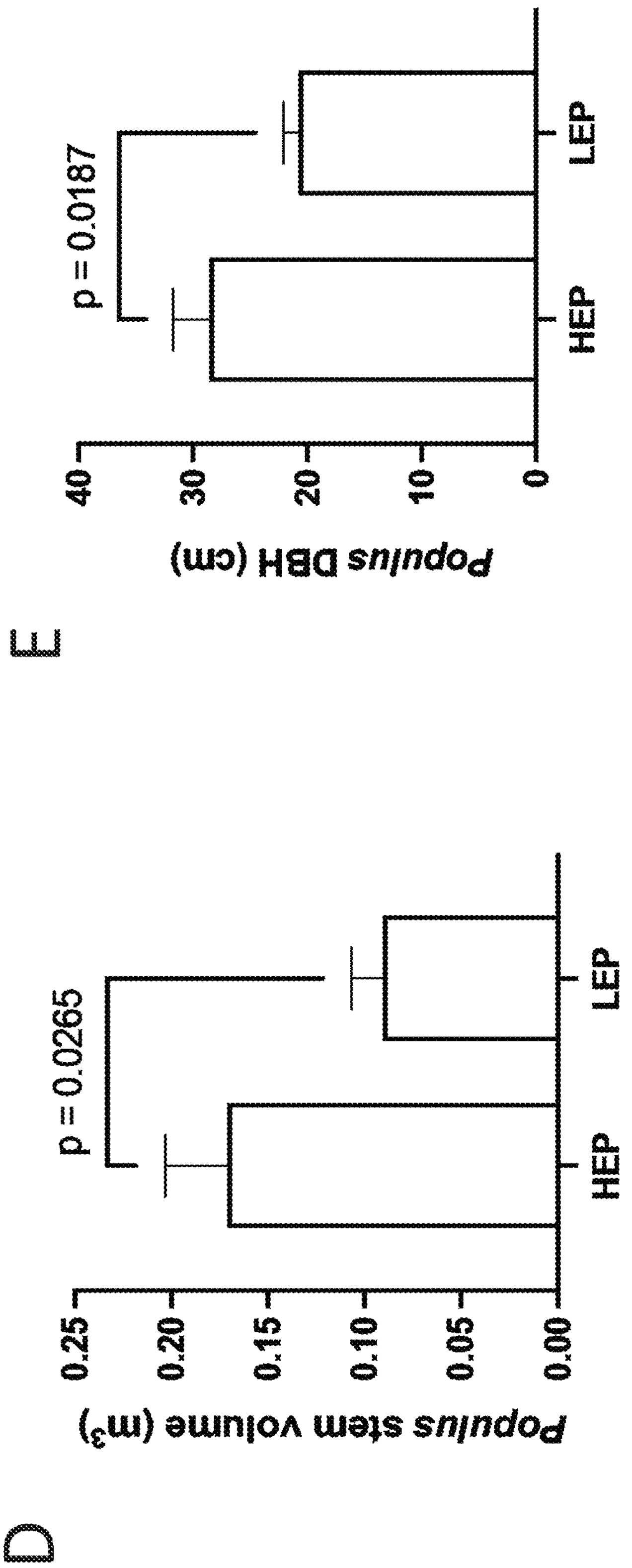
FIG. 5D-E

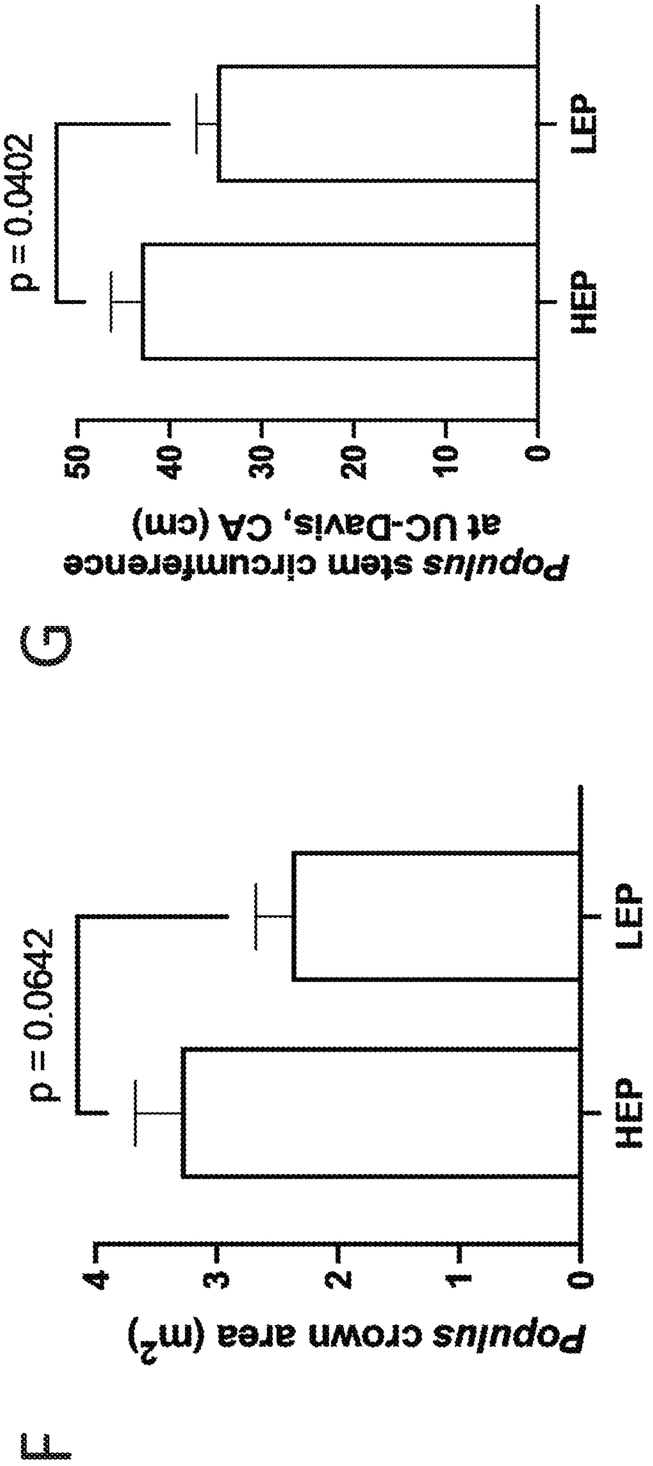
FIG. 5F-G

A

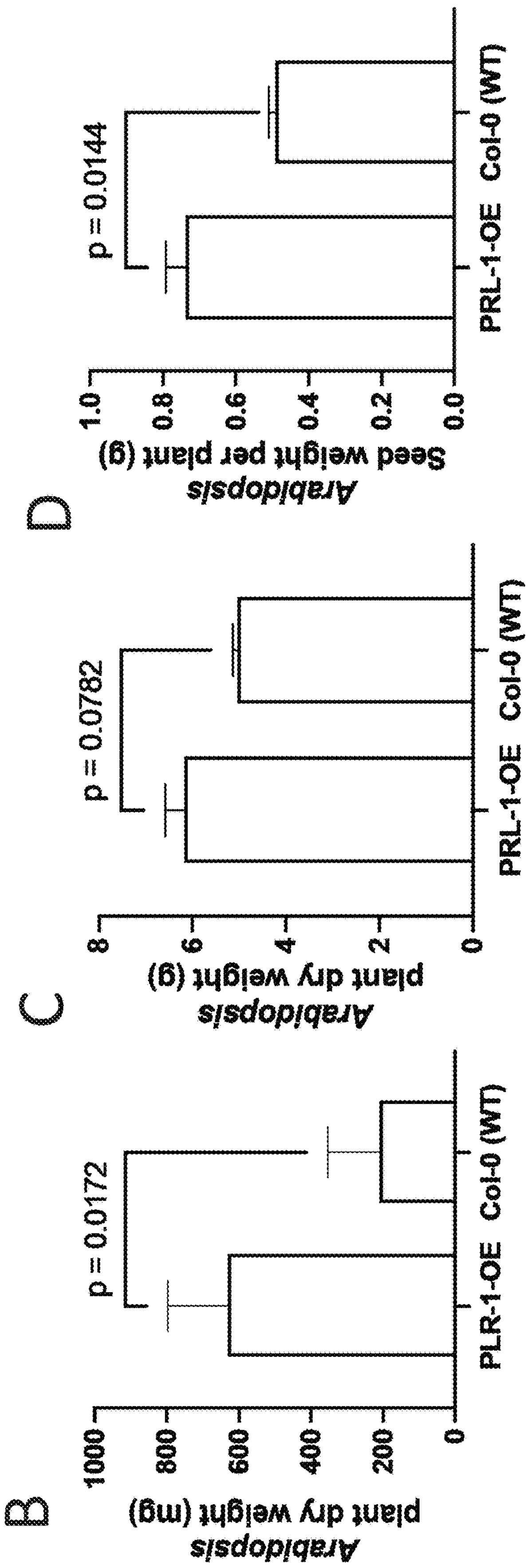
FIG. 6B-D

E

G
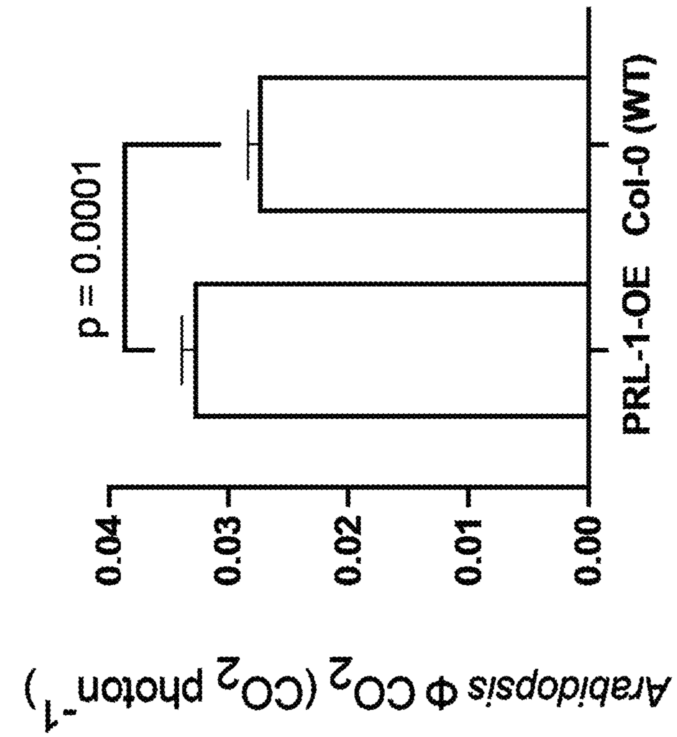
F
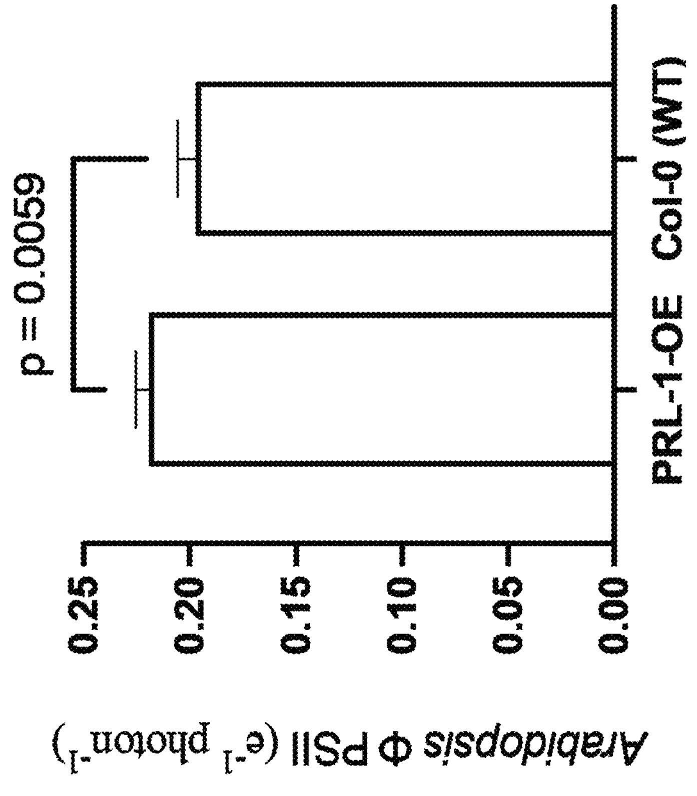
FIG. 8F-G

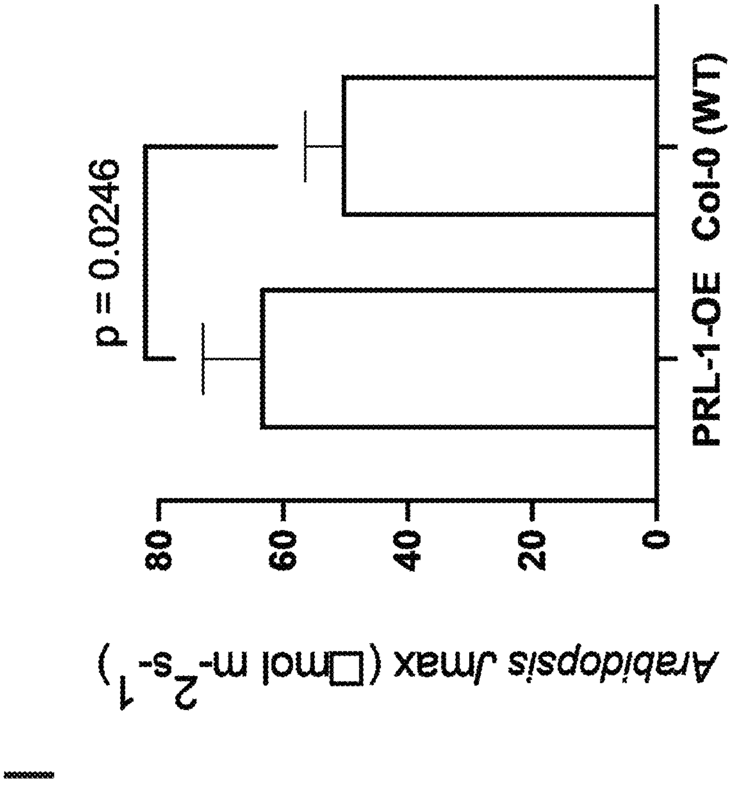
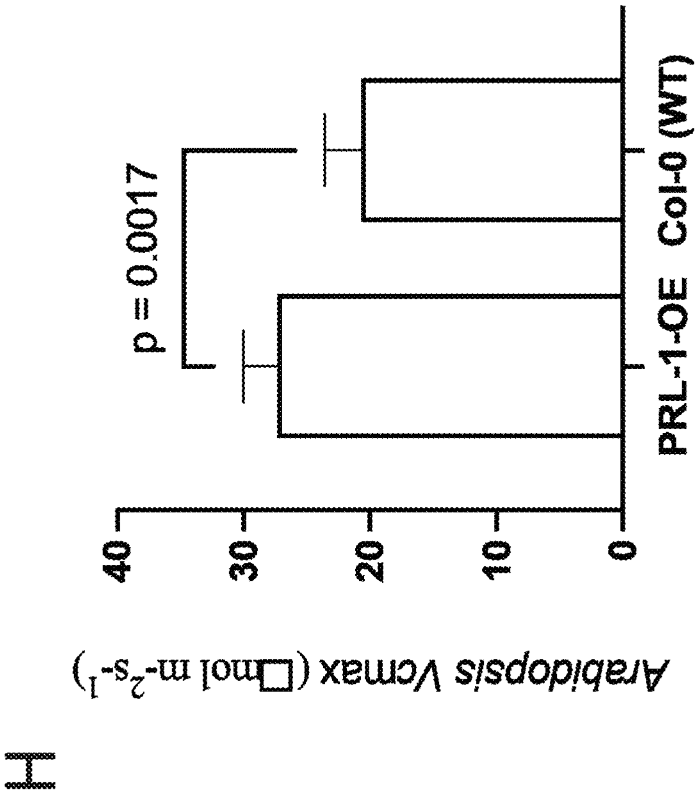
FIG. 8H-I

PLANTS WITH ENHANCED PHOTOSYNTHETIC EFFICIENCY AND BIOMASS YIELD

CROSS REFERENCE TO RELATED APPLICATION

This application claims the benefit of priority from U.S. Provisional Application No. 63/469,847, filed May 31, 2023, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 and Contract No. DE-SC0018420, both awarded by the U.S. Department of Energy. The government has certain rights in this disclosure.

INCORPORATION BY REFERENCE OF SEQUENCE LISTING

The sequence listing in the XML, named as 42455_5209_1_SequenceListing.xml of 24 KB, created on Sep. 27, 2023, and submitted to the United States Patent and Trademark Office via Patent Center, is incorporated herein by reference.

BACKGROUND

In the natural environment, plants experience a range of light intensities and spectral properties due to changes in sun angle and cloud cover in addition to shading from overlapping leaves and neighboring plants. Therefore, leaves are subjected to spatial and temporal gradients in incident light, which has major consequences for photosynthetic carbon assimilation. As light is the key resource for photosynthesis, plants acclimate to the light environment under which they are grown to maintain performance and fitness. Acclimation involves altering metabolic processes (including light harvesting and $CO_2$ capture) brought about by a range of mechanisms, from adjustments to leaf morphology to changes in photosynthetic apparatus stoichiometry, all of which impact on photosynthesis. The primary determinant of crop yield is the cumulative rate of photosynthesis over the growing season, which is regulated by the amount of light captured by the plant and the ability of the plant to efficiently use this energy to convert $CO_2$ into biomass and harvestable yield.

Under natural environmental conditions, the random duration and intensity of fluctuating light from passing clouds or leaf movements (sun and shade flecks) result in incident light intensities below light saturation that reduce photosynthetic rates, while those intensities greater than saturated lead to excess excitation energy that can result in short potential stress periods and long-term damage to leaf photosynthesis. Therefore, plants employ mechanisms that enable them to deal with these changes in excitation pressure, including thermal dissipation of excitation energy. Such processes are termed nonphotochemical quenching (NPQ) and are associated mainly with changes in the xanthophyll cycle and protonation of photosynthesis II antenna proteins, both of which are linked to the proton gradient across the thylakoid membrane.

Enhancing photosynthetic efficiency may provide an innovative route to continued improvements in plant yield. Decades of Free-air $CO_2$ enrichment (FACE) studies found a substantial increase in yield under elevated $CO_2$ in $C_3$ crops, and analysis of historic cultivars also indicated that increases in photosynthesis have unintentionally been selected for, in some crops, due to associations with yield, although there is no simple correlation due to significant variation between genotypes.

Global carbon sequestration and biomass production are regulated by a network of genes of which D-ribulose 1,5-bisphosphate carboxylase/oxygenase (Rubisco) plays a significant role as a carbon entry point to the biosphere. With an estimated 0.7 Gt, Rubisco is the most abundant protein on earth. Despite its ubiquity, Rubisco's carboxylase activity is regarded as inefficient, and its activity varies across environmental conditions. Moreover, its oxygenase activity lowers photosynthetic efficiency. On top of that, the protective dissipation of light energy, NPQ, tends to remain during the transition from light to dark, further lowering photosynthesis yield. Hence, a 10-40% yield loss is estimated due to the absence of quick photosystem recovery under fluctuating light and shade events in the plant's canopy.

One of the primary photoprotective mechanisms to fluctuating light conditions is the quick induction of NPQ on exposure to full sunlight. However, NPQ is slow to relax on return of leaves to the shade. In *Nicotiana tabacum*, a three-gene strategy involving over expression of Photosystem II subunit S (PsbS), in addition to Violaxanthin de-epoxidase (VDE) and Zeaxanthin epoxidase (ZEP), which together catalyze the interconversion between zeaxanthin and violaxanthin, resulted in 1) faster relaxation of NPQ on sun-to-shade transitions, 2) increased light use efficiency, and 3) increased biomass and yield of field grown plants. In soybean, overexpression of VDE, PsbS and ZEP led to improved NPQ relaxation increasing photosynthetic efficiency and boosting yield by 24.5% under field conditions during one season. However, this may not always be the case, as demonstrated when the same approach was taken in *Arabidopsis* and potato, leading to a decrease in growth, suggesting the interactions between conditions, species and genotype may be important in determining the universal efficacy of this strategy.

Beyond NPQ relaxation, ferredoxin-dependent and NADPH-dependent thioredoxins have also been reported to play a role in photosynthetic acclimation under fluctuating light. Ferredoxin-dependent thioredoxin mutants showed low photosynthetic efficiency under high light but performed better under low-light conditions. As crucial as rapidly relaxing NPQ upon transitioning to low light is, fast induction upon returning to high light is also vital to prevent photodamage. Hence, dynamic NPQ adjustment, which quickly acclimates to light fluctuations, could improve photosynthesis efficiency.

Plant genomes continue to evolve as they adapt to changing environmental conditions, leading to lineage-specific orphan genes. Horizontal gene transfer, domain cooption, and insertion of novel introns can contribute to some of the acquired sequences in orphan genes. Earlier, Genome-Wide Association Studies (GWAS) identified Single Nucleotide Polymorphisms (SNPs) that influence traits in *Populus trichocarpa*. Here, we screened a *P. trichocarpa* diversity panel for variation in the efficiency of photosynthesis and identified a nuclear orphan gene derived from a fragment of the plastid-encoded Rubisco large subunit that improved carbon fixation and corresponded with increased productivity in both *P. trichocarpa* and transgenic *Arabidopsis thali-*

*ana*. This provides evidence for the importance of cytoplasmic organelle to nuclear DNA transfer in the continuing source of genetic variation with the potential to drive adaptation to local environments.

SUMMARY

The current disclosure is directed to genetically modified plants, plant cells, or plant tissues wherein the genetic modification comprises expression of an exogenous nucleic acid comprising a ribulose bisphosphate carboxylase/oxygenase large subunit-related (PRL-1) gene or homolog thereof, in the plant, plant cell, or plant tissue; and wherein the expression of the exogenous nucleic acid comprising the PRL-1 gene or homolog thereof results in enhanced photosynthetic efficiency and/or plant biomass of the plant, plant cell, or plant tissue as compared to a wild-type plant, plant cell or plant tissue without the genetic modification. Additionally, the current disclosure is directed to methods of enhancing photosynthetic efficiency and biomass yield in a plant, plant cell, or plant tissue, the methods comprising expressing an exogenous nucleic acid comprising a ribulose bisphosphate carboxylase/oxygenase large subunit-related (PRL-1) gene or homolog thereof.

Certain aspects of the disclosure are directed to a genetically modified plant, plant cell, or plant tissue, wherein the genetic modification comprises expression of an exogenous nucleic acid comprising a ribulose bisphosphate carboxylase/oxygenase large subunit-related (PRL-1) gene or homolog thereof, in the plant, plant cell, or plant tissue; and wherein the expression of the exogenous nucleic acid comprising the PRL-1 gene or homolog thereof results in enhanced photosynthetic efficiency and/or plant biomass of the plant, plant cell, or plant tissue as compared to a wild-type plant, plant cell or plant tissue without the genetic modification. In some embodiments, the expression of the exogenous nucleic acid comprising the PRL-1 gene or homolog thereof results in enhanced photosynthetic efficiency and/or plant biomass of the plant, plant cell, or plant tissue as compared to a wild-type plant, plant cell or plant tissue without the genetic modification when exposed to a stable or a fluctuating light environment. In some embodiments, the PRL-1 gene or homolog thereof comprises a sequence having at least 90% nucleotide sequence identity to SEQ ID NO: 1. In some embodiments, the PRL-1 gene or homolog thereof encodes a protein comprising an amino acid sequence having at least 90% sequence identity to SEQ ID NO: 2. In some embodiments, the PRL-1 gene in the exogenous nucleic acid is operable linked to a heterologous promoter. In some embodiments, the heterologous promoter is a constitutive promoter. In some embodiments, the heterologous promoter is a tissue-specific promoter. In some embodiments, the heterologous promoter is a native promoter. In some embodiments, the exogenous nucleic acid is stably transfected or transformed into the plant genome. In some embodiments, the plant is selected from the group consisting of genera Acer, Afzelia, *Allium, Arabidopsis, Agrostis, Avena, Betula, Brassica, Capsicum, Citrullus, Cucumis, Eucalyptus, Fagus, Festuca, Fraxinus*, Fragaria, Glycine, *Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

Some aspects of the current disclosure are directed to methods of enhancing photosynthetic efficiency and biomass yield in a plant, plant cell, or plant tissue, the methods comprising expressing an exogenous nucleic acid comprising a ribulose bisphosphate carboxylase/oxygenase large subunit-related (PRL-1) gene or homolog thereof, in the plant, plant cell, or plant tissue, wherein the expression of the exogenous nucleic acid comprising the PRL-1 gene or homolog thereof results in enhanced photosynthetic and/or plant biomass of the plant, plant cell, or plant tissue as compared to a wild-type plant, plant cell or plant tissue without the genetic modification. In some embodiments, the expression of the exogenous nucleic acid comprising the PRL-1 gene or homolog thereof results in enhanced photosynthetic efficiency and/or plant biomass of the plant, plant cell, or plant tissue as compared to a wild-type plant, plant cell or plant tissue without the genetic modification when exposed to a stable or a fluctuating light environment. In some embodiments, the exogenous nucleic acid comprises a sequence having at least 90% sequence identity to SEQ ID NO: 1. In some embodiments, the PRL-1 gene encodes a protein comprising an amino acid sequence having at least 90% sequence identity to SEQ ID No: 2. In some embodiments, the PRL-1 gene in the exogenous nucleic acid is operable linked to a heterologous promoter. In some embodiments, the heterologous promoter is a constitutive promoter. In some embodiments, the heterologous promoter is a tissue specific promoter. In some embodiments, the heterologous promoter is a native promoter (some examples of suitable promoters). In some embodiments, the exogenous nucleic acid is stably transfected or transformed into the plant genome. In some embodiments, the plant is selected from the group consisting of genera Acer, Afzelia, *Allium, Arabidopsis, Agrostis, Avena, Betula, Brassica, Capsicum, Citrullus, Cucumis, Eucalyptus, Fagus, Festuca, Fraxinus*, Fragaria, Glycine, *Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A-D Orphan-moonlighting gene PRL-1 is localized in the nucleus, plastid, and endoplasmic reticulum. Uniquely acquired nucleotide sequences likely from *Streptomyces* sp. and Trachymyrmex s. at the N-terminus in two exons while keeping one-third of the regular RbcL sequence at the c-terminus, (B) Presence of the two unique exons at the N-terminus are responsible for the formation of alpha helix structure (right), (C) In vivo subcellular localization of PRL-1-eGFP in *Nicotiana benthamiana* leaves after 72 hrs of infiltration, (D) Immunoblot showing the accumulation of PRL-1 both in nuclear and non-nuclear fractions of *P. trichocarpa* protoplast. In (B), protein modeling was made using Protein Homology/analogY Recognition Engine V 2.0 (Phyre2) (www.sbg.bio.ic.ac.uk) platform using default parameters. In (C), *N. benthamiana* leaves are co-infiltrated with PRL-1-eGFP in combination with either Nuclear-mCherry marker (Addgene #61168) in the upper (C) panel, or plastid-mCherry marker (TAIR #CD3-999) in the middle (C) panels, or Endoplasmic Reticulum (ER)-mCherry marker (TAIR #CD3-960) in the lower (C) panel, respectively. Yellow arrows in the upper, middle, and lower panels of (C) indicates nuclear, plastid and ER localizations, respectively, while white arrows indicate PRL-1. In (D), fractionated *P. trichocarpa* protoplast were subjected to immunoblotting using anti-GFP (enQuirebio, QAB10298), anti-histone (abcam, #ab1791), and anti-UGPase (Agrisera, #AS05 086), primary antibodies followed by anti-rabbit secondary antibody (Agrisera AS09 602; 1:10000) and treated with ECL substrate (Promega Cat. #W1001).

FIG. 3A-E PRL-1 has transcriptional repressor activity and interacts with photosynthesis regulatory elements in a light-dependent manner. (A) PRL-1 has no activator activity, (B) PRL-1 has repressor activity, (C) Silver-stained SDS-PAGE gel following immunoprecipitation, (D) Ven diagram illustrating IP-MS detected proteins interacting with PRL-1 from high light and dark-exposure, (E) Selected normalized protein abundance fold-changes between dark and light exposures. In (A), In the reporter construct (Ga14: GUS), the GUS reporter gene was fused downstream of the Ga14 DNA binding site. The construct GD-PRL-1-TF was used to express Ga14 binding domain (GD) fused with PRL-1. The construct expressing GD fused with GFP was used as the negative control. Transactivator GD-VP16 was used as the positive control. In (B), PRL-1 represses the expression of the GUS reporter activated by the transactivator LD-VP16, in which the transcription activator VP16 is fused with LexA binding domain (LD). In the reporter construct (LexA-Ga14: GUS), the GUS reporter gene was fused downstream of the LexA DNA binding site and Ga14 DNA binding site. The construct only expressing GD was used as the negative control. Luciferase activity was used to normalize and calculate the relative GUS activity and the 35S: Luciferase construct was co-transfected with reporters and effectors. In (C), “wash” represents final eluent prior to elution, “light”: plants exposed to 2000 μmol $S^{-1}$ $m^{-2}$ sun light intensity for 10 minutes, “Dark”: Plants exposed to darkness for 10 minutes following the light treatment.

FIG. 5A-G shows the enhanced plant yield attributes in PRL-1 expression. (A) Shows six-months-old *P. trichocarpa* plants with high (left) and low (right) expression levels of PRL-1. (B) Shows *Populus* plant height growing at the greenhouse, and (C) field conditions in Placerville, CA. (D) Shows stem volume in plants grown at Placerville, CA. (E) Shows stem diameter at breast height, DBH, in plants grown at Clatskanie, Oregon. (F) shows the crown area of selected 17 genotypes from HEP and LEP under field conditions grown at Placerville, CA. (G) Shows basal circumference from HEP and LEP genotypes grown under field conditions at UC-Davis, CA. ‘KTMA-12-4’, ‘BESC-379’, and ‘BESC-39’ represented HEP genotypes at the green house while ‘BESC-870’, ‘BESC-67’, and ‘HARA-26-2’ from LEP genotypes.

FIG. 6A-F PRL-1 enhances *Arabidopsis* biomass and seed yield. (A) *Arabidopsis* independent transgenic events expressing PRL-1. Where (B) shows *Arabidopsis* plant dry biomass per plant growing in long-day and (C) represents short day conditions. (D) Shows *Arabidopsis* seed yield per plant. (E) Illustrates a plasmid of PRL-1-eGFP construct used to transform *Arabidopsis*. (F) Represents the relative transcript level of PRL-1 in independent transgenic *Arabidopsis* events. Pooled data are used in (B), (C), and (D) for *Arabidopsis* independent transgenic events. Long-day and short-day growing conditions in ‘B’ and ‘C’ corresponds to 16/8 and 8/16 of light/dark exposures, respectively.

FIG. 8A-I PRL-1 contributes to a dynamic NPQ response to fluctuating light and photosynthesis efficiency in *Populus* and *Arabidopsis*. (A) Non-photochemical quenching (NPQ) measurements of leaves exposed to fluctuating light intensities, (B) Quantum efficiency of linear electron transport (Φ PSII), and (C) Quantum efficiency of $CO_2$ assimilation ($CO_2$) under fluctuating light in *P. trichocarpa* HEP and LEP genotypes. (D) Shows the maximum rate of Rubisco carboxylase activity (Vcmax). (E) Shows the maximum rate of photosynthetic electron transport (Jmax) in *P. trichocarpa*. (F) Shows the quantum efficiency of linear electron transport (Φ PSII) and (G) shows the quantum efficiency of $CO_2$ assimilation ($CO_2$) under fluctuating light in *Arabidopsis*. (H) Shows the maximum rate of Rubisco carboxylase activity (Vcmax) and (I) represents the maximum rate of photosynthetic electron transport (Jmax) in *Arabidopsis* overexpressing PRL-1. P values in (B), (C), (D) and (E) are adjusted values from Dunnett’s multiple comparison test following ANOVA. P values in (F), (G), (H), and (I) are from simple pairwise comparison test. n=5 for (A) while n=3 in (B)-€, n=4 (F)-(I). Pooled data are used in (F), (G), (H), and (I) for *Arabidopsis* independent transgenic events. In (A) to (E), HEP genotypes are represented by KTMA-12-4, BESC-39, and BESC-379, while BEC-870, BESC-67, and HARA26-2 represent LEP genotypes.

DETAILED DESCRIPTION

Figure 1C:
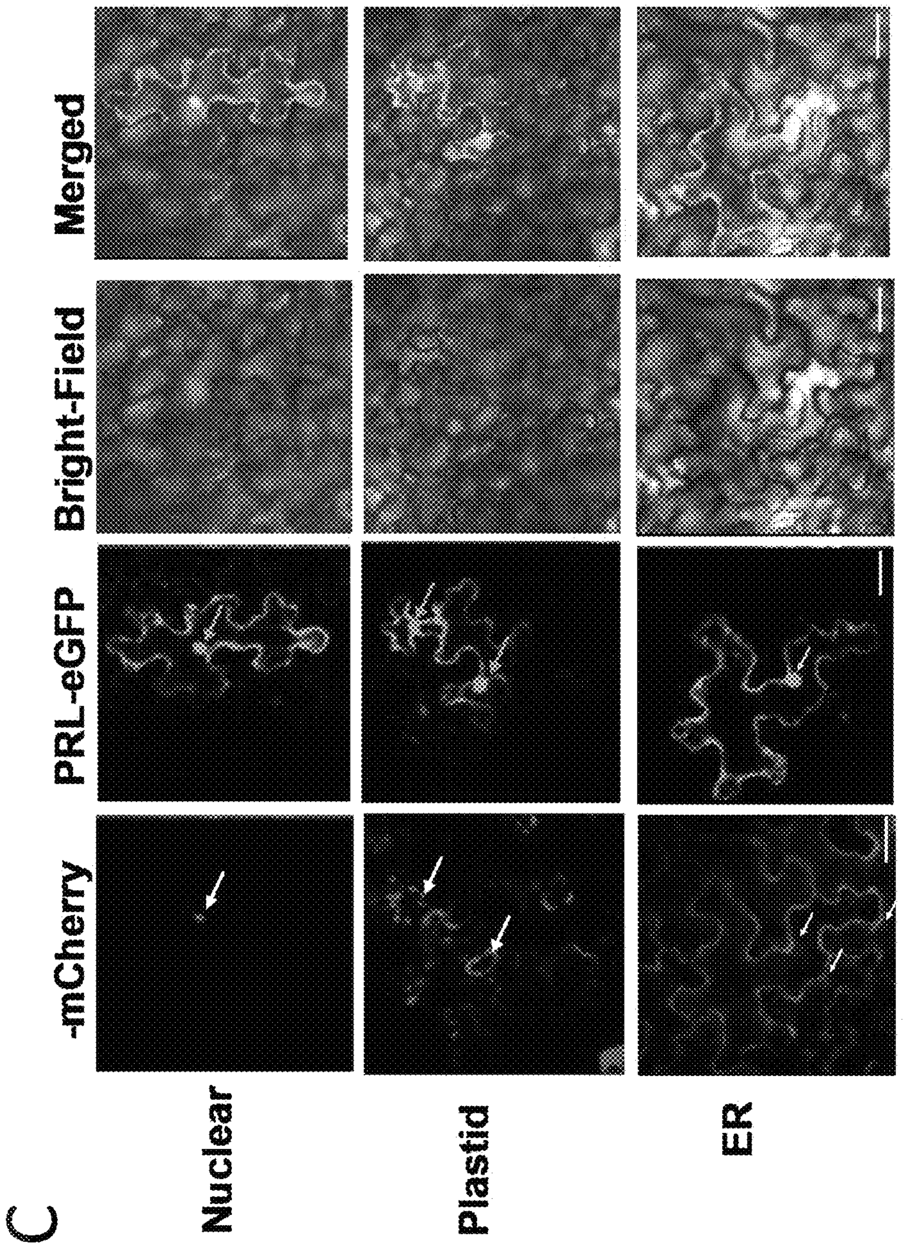

Although claimed subject matter will be described in terms of certain examples, other examples, including examples that do not provide all the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include the lower limit value, the upper limit value, and all values between the lower limit value and the upper limit value, including, but not limited to, all values to the magnitude of the smallest value (either the lower limit value or the upper limit value).

“Complementary” or “substantially complementary” refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95% (e.g., at least 90%, at least 91%, at least 92%, at least 93%, at least 94%, and at least 95%), and even at least about 98% to about 100% (e.g., at least 98%, at least 99%, and 100%).

“Hybridization” refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of approximately up to 1M, often up to about 500 mM and may be up to about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a primer will hybridize to its target subsequence but will not hybridize to the other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01 M to no more than 1M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized.

"Nucleic acid", "oligonucleotide", "oligo" or grammatical equivalents used herein refers generally to at least two nucleotides covalently linked together. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, DNA: DNA hybrids can exhibit higher stability in some environments.

As used herein, the phrase "exogenous polynucleotide" refers to a heterologous nucleic acid sequence which may not be naturally expressed within the plant (e.g., a nucleic acid sequence from a different species) or which overexpression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

The term "endogenous" as used herein refers to any polynucleotide or polypeptide which is present and/or naturally expressed within a plant or a cell thereof.

"Primer" means an oligonucleotide, either natural or synthetic, that, upon forming a duplex with a polynucleotide template, can act as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

The term "homolog" or "homologous" means a gene related to a second gene by descent from a common ancestral DNA sequence, therefore, the corresponding polynucleotide/polypeptide has a certain degree of homology, i.e., sequence identity (at least 40%, 60%, 65%, at least 66%, 68%, 70%, 75%, 80%, 86%, 88%, 90%, 92%, 95%, 97% or 99% sequence identity). A "homolog" furthermore means that the function is equivalent to the function of the original gene. Homologs of a given gene and corresponding or equivalent positions in the homologous genes or proteins can be determined by sequence alignment programs, e.g., including but not limited to, NCBI BLAST, ClustalW, DIAMOND, CS-BLAST, and MAFFT.

Homologous sequences include both orthologous and paralogous sequences. The term "paralogous" relates to gene-duplications within the genome of a species leading to paralogous genes. The term "orthologous" relates to homologous genes in different organisms due to ancestral relationship. Thus, orthologs are evolutionary counterparts derived from a single ancestral gene in the last common ancestor of given two species and therefore have great likelihood of having the same function. Homology (e.g., percent homology, sequence identity sequence similarity) can be determined using any homology comparison software computing a pairwise sequence alignment.

Some embodiments of the disclosure encompass fragments of the described polypeptides and polypeptides having mutations, such as deletions, insertions or substitutions of one or more amino acids, either naturally occurring or man induced, either randomly or in a targeted fashion.

As used herein, "nonconservative mutation" refers to a change in a DNA or RNA sequence that results in the replacement of an amino acid with one that is not biochemically similar. In some embodiments, a nonconservative mutation of a cysteine residue comprises changing the cysteine residue to any amino acid other than serine, selenocysteine, threonine, and methionine (because serine, selenocysteine, threonine, and methionine are biochemically similar to cysteine). In some embodiments, the non-silent mutation is a nonconservative mutation. In some embodiments, the nonconservative mutation is a cysteine to alanine mutation.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

According to some embodiments of the disclosure, the promoter is heterologous to the isolated polynucleotide and/or to the host cell. As used herein the phrase "heterologous promoter" refers to a promoter from a different species or from the same species but from a different gene locus as of the isolated polynucleotide sequence.

According to some embodiments of the disclosure, the isolated polynucleotide is heterologous to the plant cell e.g., the polynucleotide is derived from a different plant species when compared to the plant cell, thus the isolated polynucleotide and the plant cell are not from the same plant species.

According to some embodiments of the disclosure, the promoter is a plant promoter, which is suitable for expression of the exogenous polynucleotide in a plant cell.

Any suitable promoter sequence can be used by the nucleic acid construct of the present disclosure. In some embodiments, the promoter is a constitutive promoter, a tissue-specific promoter, or an inducible promoter. A constitutive promoter directs the expression of a gene in all tissues of a plant during the various stages of development. A tissue-specific promoter directs expression of the gene only in certain tissues and may or may not be activated during all stages of development. An inducible promoter initiates gene expression in response to chemical, physical or biotic and abiotic stresses.

Suitable constitutive promoters include, for example, CaMV 35S promoter, CmYLCV, *Rubi*3, *Mirabilis* MV 24, MpEF1alpha, PJJ 35S from *Brachypodium, Arabidopsis* At6669 promoter, maize Ub1 promoters, rice actin 1, pEMU, CaMV 19S, rice GOS2 promoters, RBCS promoter, rice cyclophilin, maize H3 histone, actin 2, and Synthetic Super MAS.

The use of organ or tissue specific promoters that induce and specifically control the expression of transgenes in organ and/or tissue may be advantageous to avoid a waste of energy and nutrients from the transgenic plant when the protein of interest is not necessary for the whole plant. There are promoters for specific tissues or organs of plants ranging from seed specific promoters, leaf and vascular tissue specific promoters, fruit specific promoters, pollen specific promoters, and root specific promoters. Suitable tissue-specific promoters include, but are not limited to, leaf-specific promoters, e.g., AT5G06690 (Thioredoxin), AT5G61520 (AtSTP3), PD540, Zmglpl, and pnGLP promoters.

As used herein, "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated as known in the art.

Identity (e.g., percent homology) can be determined using any homology comparison software, including for example, the BlastN software of the National Center of Biotechnology information (NCBI) such as by using default parameters.

In some embodiments, the disclosure is directed to a genetically modified plant, plant cell, or plant tissue, wherein the genetic modification comprises expression of an exogenous nucleic acid comprising a ribulose bisphosphate carboxylase/oxygenase large subunit-related (PRL-1) gene or homolog thereof, in the plant, plant cell, or plant tissue; and wherein the expression of the exogenous nucleic acid comprising the PRL-1 gene or homolog thereof results in enhanced photosynthetic efficiency and/or plant biomass of the plant, plant cell, or plant tissue as compared to a wild-type plant, plant cell or plant tissue without the genetic modification.

As used herein, "photosynthetic efficiency" is the fraction of light energy converted into chemical energy during photosynthesis in green plants and algae. There are a number of traits known in the art which are used in order to measure photosynthetic efficiency. Some non-limiting examples of such traits include plant yield, biomass, growth rate, plant vigor, and seed yield, among others. "Plant yield" refers to the amount (e.g., as determined by weight or size) or quantity (numbers) of tissues or organs produced per plant or per growing season.

As used herein, "plant biomass" refers to the amount measured in grams of air-dry tissue of a tissue produced from the plant in a growing season, which could also determine or affect the plant yield or the yield per growing area. An increase in plant biomass can be in the whole plant or in parts thereof such as aboveground (harvestable) parts, vegetative biomass, roots, and seeds.

As used herein, "growth rate" refers to the increase in plant organ/tissue size per time (can be measured in $cm^2$ per day or cm/day).

As used herein, "photosynthetic capacity" (also known as "Amax") is a measure of the maximum rate at which leaves are able to fix carbon during photosynthesis. It is typically measured as the amount of carbon dioxide that is fixed per square meter per second, for example as $\mu mol\ m^{-2}\ sec^{-1}$. Plants are able to increase their photosynthetic capacity by several modes of action, such as by increasing the total leaves area e.g., by increase of leaves area, increase in the number of leaves, and increase in plant's vigor, e.g., the ability of the plant to grow new leaves along a time course, as well as by increasing the ability of the plant to efficiently execute carbon fixation in the leaves. Hence, the increase in total leaves area can be used as a reliable measurement parameter for photosynthetic capacity increment.

As used herein, "plant vigor" refers to the amount (measured by weight) of tissue produced by the plant over a given period of time. Increased vigor could determine or affect the plant yield or the yield per growing time or growing area. Additionally, early vigor (seed and/or seedling) results in improved field stand.

It should be noted that a plant trait such as yield, growth rate, biomass, vigor, oil content, fiber yield, fiber quality, fiber length, photosynthetic capacity, fertilizer use efficiency (e.g., nitrogen use efficiency) can be determined under stress (e.g., abiotic stress, nitrogen-limiting conditions) and/or non-stress (normal) conditions.

As used herein, the phrase "non-stress conditions" refers to the growth conditions (e.g., water, temperature, light-dark cycles, humidity, salt concentration, fertilizer concentration in soil, nutrient supply such as nitrogen, phosphorous and/or potassium), that do not significantly go beyond the everyday climatic and other abiotic conditions that plants may encounter, and which allow optimal growth, metabolism, reproduction and/or viability of a plant at any stage in its life cycle (e.g., in a crop plant from seed to a mature plant and back to seed again). Those skilled in the art are aware of normal soil conditions and climatic conditions for a given plant in a given geographic location. While the non-stress conditions may include some mild variations from the optimal conditions (which vary from one type/species of a plant to another), such variations do not cause the plant to cease growing without the capacity to resume growth.

The phrase "abiotic stress" as used herein refers to any adverse effect on metabolism, growth, reproduction and/or viability of a plant. Accordingly, abiotic stress can be induced by suboptimal environmental growth conditions such as, for example, salinity, osmotic stress, water deprivation, drought, flooding, freezing, low or high temperature, heavy metal toxicity, anaerobiosis, nutrient deficiency (e.g., nitrogen deficiency or limited nitrogen), atmospheric pollution or UV irradiation. The implications of abiotic stress are discussed in the Background section.

The phrase “abiotic stress tolerance” as used herein refers to the ability of a plant to endure an abiotic stress without suffering a substantial alteration in metabolism, growth, productivity and/or viability.

The term “fiber” is usually inclusive of thick-walled conducting cells such as vessels and tracheids and to fibrillar aggregates of many individual fiber cells. Hence, the term “fiber” refers to (a) thick-walled conducting and non-conducting cells of the xylem; (b) fibers of extraxylary origin, including those from phloem, bark, ground tissue, and epidermis; and (c) fibers from stems, leaves, roots, seeds, and flowers or inflorescences (such as those of *Sorghum vulgare* used in the manufacture of brushes and brooms).

Example of fiber producing plants, include, but are not limited to, agricultural crops such as cotton, silk cotton tree (Kapok, *Ceiba pentandra*), desert willow, creosote bush, winterfat, balsa, kenaf, roselle, jute, sisal abaca, flax, corn, sugar cane, hemp, ramie, kapok, coir, bamboo, spanish moss and Agave spp. (e.g. sisal).

As used herein the term “increasing” refers to at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, increase in the trait [e.g., yield, seed yield, biomass, growth rate, vigor, oil content, fiber yield, fiber quality, fiber length, photosynthetic capacity, abiotic stress tolerance, and/or nitrogen use efficiency] of a plant as compared to a native plant or a wild type plant [i.e., a plant not modified with the biomolecules (polynucleotide or polypeptides) of the disclosure, e.g., a non-transformed plant of the same species which is grown under the same (e.g., identical) growth conditions].

The phrase “expressing an exogenous polynucleotide” as used herein refers to the expression of an exogenous polynucleotide within the plant by introducing the exogenous polynucleotide into a plant cell or plant and expressing by recombinant means, which are known in the art. As used herein, “expressing” refers to expression at the mRNA and optionally polypeptide level.

In some embodiments, enhanced photosynthetic efficiency is determined by photosynthetic yield. In some embodiments, plant vigor is used to determine photosynthetic yield, where plant vigor is calculated by measuring the increase in growth parameters such as leaf area, fiber length, rosette diameter, plant fresh weight, and the like per time.

In some embodiments, growth rate is used to determine photosynthetic yield. The growth rate can be measured using digital analysis of growing plants. For example, images of plants growing in greenhouse on plot basis can be captured every 3 days and the rosette area can be calculated by digital analysis. Rosette area growth is calculated using the difference of rosette area between days of sampling divided by the difference in days between samples.

In photosynthesis, light-driven redox chemistry of the electron transport chain and temperature-dependent enzymatic reactions of the Calvin-Benson cycle are tightly coupled. Any limitation in one of these two major parts of photosynthesis will have an immediate impact also on the other one. Therefore, the efficiency of the photosynthetic process is highly dependent on the ambient conditions in the respective habitat. Changes in various abiotic factors, such as intensity and quality of incident light, temperature, and nutrient and water availability affect the photosynthetic yield. Light is one of the most important environmental factors for a photosynthetic organism. As a result of various abiotic and biotic influences, light is highly variable in its intensity and its quality on both a short-term timescale (in the range of seconds to minutes) and a long-term timescale (in the range of hours, days, and seasons).

In some embodiments, enhanced plant biomass is determined by factors known in the art. Examples of such factors include but are not limited to stem diameter, crown area, plant height, and LiDAR-based biomass estimation.

In some embodiments, the genetically modified plant, plant cell, or plant tissue expressing the exogenous nucleic acid comprising the PRL-1 gene or homolog thereof results in enhanced photosynthetic efficiency and/or plant biomass of the plant, plant cell, or plant tissue as compared to a wild-type plant, plant cell or plant tissue without the genetic modification when the plants are exposed to a stable or a fluctuating light environment. As used herein, a “stable light environment” is considered light conditions with constant intensities and simple light patterns. As used herein, “fluctuating light environment” is known to one of skill in the art, essentially any number of changes to a stable light environment. Briefly, fluctuating light environments can include constant intensities of light that can be swapped to a simple light pattern consisting of one or more step changes in intensity or different frequencies. However, the dynamics of the fluctuations can be varied.

In some embodiments of the disclosure, the plant is a dicotyledonous plant.

In some embodiments of the disclosure, the plant is a monocotyledonous plant.

In some embodiments, the disclosure provides a plant, plant cell, or plant tissue exogenously expressing the polynucleotide of some embodiments of the disclosure, the nucleic acid construct of some embodiments of the disclosure and/or the polypeptide of some embodiments of the disclosure. According to some embodiments of the disclosure, expressing the exogenous polynucleotide of the disclosure within the plant is affected by transforming one or more cells of the plant with the exogenous polynucleotide, followed by generating a mature plant from the transformed cells and cultivating the mature plant under conditions suitable for expressing the exogenous polynucleotide within the mature plant.

The nucleic acid construct of some embodiments of the disclosure can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants known to those having skill in the art. The principal methods of causing stable integration of exogenous DNA into plant genomic DNA include: *Agrobacterium*-mediated gene transfer, Direct DNA uptake, and targeted genome engineering.

The *Agrobacterium* system, also called “floral dip method”, includes the use of plasmid vectors that contain defined DNA segments that integrate into the plant genomic DNA through inflorescence. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Targeted genome engineering (also known as genome editing) has emerged as an alternative to classical plant breeding and transgenic (Genetically Modified Organism-GMO) methods to improve crop plants. Available methods for introducing site-specific double strand DNA breaks include zinc finger nucleases (ZFNs), TAL effector nucleases (TALENs) and CRISPR/Cas system. ZFNs are reviewed in Carroll, D. (Genetics, 188.4 (2011): 773-782), and TALENs are reviewed in Zhang et al. (*Plant Physiology,* 161.1 (2013): 20-27), which are incorporated herein in their entirety.

CRISPR/Cas system is a method based on the bacterial type II CRISPR (clustered regularly interspaced short palindromic repeats)/Cas (CRISPR-associated) immune system. The CRISPR/Cas system allows targeted cleavage of genomic DNA guided by a customizable small noncoding RNA, resulting in gene modifications by both non-homologous end joining (NHEJ) and homology-directed repair (HDR) mechanisms. Belhaj et al. (*Plant Methods,* 2013, 9:39) summarizes and discusses applications of the CRISPR/Cas technology in plants and is incorporated herein in its entirety.

In some embodiments, genome editing is achieved by CRISPR (Clustered regularly-interspaced short palindromic repeats)/Cas technology. CRISPR-Cas and similar gene targeting systems are well known in the art with reagents and protocols readily available. Exemplary genome editing protocols are described in Jennifer Doudna, and Prashant *Mali, "CRISPR-Cas: A Laboratory Manual*" (2016) (CSHL Press, ISBN: 978-1-621821-30-4) and Ran, F. Ann, et al. (*Nature Protocols* (2013), 8 (11): 2281-2308).

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different, and each seed will grow a plant with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced from the seedlings to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the disclosure, the transformation is affected by introducing to the plant cell a nucleic acid construct which includes the exogenous polynucleotide of some embodiments of the disclosure and at least one promoter for directing transcription of the exogenous polynucleotide in a host cell (a plant cell).

Once expressed within the plant cell, plant tissue, or the entire plant, the level of the polypeptide encoded by the exogenous polynucleotide can be determined by methods well known in the art such as, activity assays, Western blots using antibodies capable of specifically binding the polypeptide, Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-in situ hybridization.

In some embodiments, the exogenous nucleic acid comprises a sequence having at least 90% sequence identity to SEQ ID NO: 1. In some embodiments, the exogenous nucleic acid comprises a sequence having at least 91% sequence identity to SEQ ID NO: 1. In some embodiments, the exogenous nucleic acid comprises a sequence having at least 92% sequence identity to SEQ ID NO: 1. In some embodiments, the exogenous nucleic acid comprises a sequence having at least 93% sequence identity to SEQ ID NO: 1. In some embodiments, the exogenous nucleic acid comprises a sequence having at least 94% sequence identity to SEQ ID NO: 1. In some embodiments, the exogenous nucleic acid comprises a sequence having at least 95% sequence identity to SEQ ID NO: 1. In some embodiments, the exogenous nucleic acid comprises a sequence having at least 96% sequence identity to SEQ ID NO: 1. In some embodiments, the exogenous nucleic acid comprises a sequence having at least 97% sequence identity to SEQ ID NO: 1. In some embodiments, the exogenous nucleic acid comprises a sequence having at least 98% sequence identity to SEQ ID NO: 1. In some embodiments, the exogenous nucleic acid comprises a sequence having at least 99% sequence identity to SEQ ID NO: 1. In some embodiments, the exogenous nucleic acid is set forth by SEQ ID NO: 1.

In some embodiments, the exogenous PRL-1 gene or homolog thereof encodes a polypeptide comprising an amino acid sequence having at least about 90% sequence identity to SEQ ID NO: 2. In some embodiments, the exogenous PRL-1 gene or homolog thereof encodes a polypeptide comprising an amino acid sequence having at least about 91% sequence identity to SEQ ID NO: 2. In some embodiments, the exogenous PRL-1 gene or homolog thereof encodes a polypeptide comprising an amino acid sequence having at least about 93% sequence identity to SEQ ID NO: 2. In some embodiments, the exogenous PRL-1 gene or homolog thereof encodes a polypeptide comprising an amino acid sequence having at least about 94% sequence identity to SEQ ID NO: 2. In some embodiments, the exogenous PRL-1 gene or homolog thereof encodes a polypeptide comprising an amino acid sequence having at least about 94% sequence identity to SEQ ID NO: 2. In some embodiments, the exogenous PRL-1 gene or homolog thereof encodes a polypeptide comprising an amino acid sequence having at least about 95% sequence identity to SEQ ID NO: 2. In some embodiments, the exogenous PRL-1 gene or homolog thereof encodes a polypeptide comprising an amino acid sequence having at least about 96% sequence identity to SEQ ID NO: 2. In some embodiments, the exogenous PRL-1 gene or homolog thereof encodes a polypeptide comprising an amino acid sequence having at least about 97% sequence identity to SEQ ID NO: 2. In some embodiments, the exogenous PRL-1 gene or homolog thereof encodes a polypeptide comprising an amino acid sequence having at least about 98% sequence identity to SEQ ID NO: 2. In some embodiments, the exogenous PRL-1 gene or homolog thereof encodes a polypeptide comprising an amino acid sequence having at least about 99% sequence identity to SEQ ID NO: 2. In some embodiments, the exogenous PRL-1 gene or homolog thereof encodes a polypeptide comprising an amino acid sequence set forth by SEQ ID NO: 2.

In some embodiments of the disclosure, the PRL-1 gene in the exogenous nucleic acid is operably linked to a heterologous promoter. A coding nucleic acid sequence is "operably linked" to a regulatory sequence (e.g., promoter) if the regulatory sequence is capable of exerting a regulatory effect on the coding sequence to which it is linked.

In some embodiments, the heterologous promoter is a constitutive promoter. In some embodiments, the heterologous promoter is a tissue specific promoter. In some embodiments, the heterologous promoter is a plant promoter. In some embodiments, the promoter is a tissue specific promoter. Examples of promoters suitable for use are provided above in this disclosure.

In some embodiments, the exogenous nucleic acid is stably transfected or transformed into the plant genome. In stable transformation, the exogenous polynucleotide is integrated into the plant genome and as such it represents a stable and inherited trait.

In some embodiments, the genetically modified plant, plant cell or plant tissue is selected from the group consisting of genera Acer, Afzelia, *Allium, Arabidopsis, Agrostis, Avena, Betula, Brassica, Capsicum, Citrullus, Cucumis, Eucalyptus, Fagus, Festuca, Fraxinus*, Fragaria, Glycine, *Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

Certain aspects of the current disclosure are directed to methods of enhancing photosynthetic efficiency and biomass yield in a plant, plant cell, or plant tissue, the methods comprising expressing an exogenous nucleic acid comprising a ribulose bisphosphate carboxylase/oxygenase large subunit-related (PRL-1) gene or homolog thereof, in the plant, plant cell, or plant tissue, wherein the expression of the exogenous nucleic acid comprising the PRL-1 gene or homolog thereof results in enhanced photosynthetic and/or plant biomass of the plant, plant cell, or plant tissue as compared to a wild-type plant, plant cell or plant tissue without the genetic modification.

In some embodiments, the expression of the exogenous nucleic acid comprising the PRL-1 gene or homolog thereof results in enhanced photosynthetic efficiency and/or plant biomass of the plant, plant cell, or plant tissue as compared to a wild-type plant, plant cell or plant tissue without the genetic modification when exposed to a stable or a fluctuating light environment.

In some embodiments, the exogenous nucleic acid comprises a sequence having at least 90% sequence identity to SEQ ID NO: 1. In some embodiments, the exogenous nucleic acid comprises a sequence having at least 91% sequence identity to SEQ ID NO: 1. In some embodiments, the exogenous nucleic acid comprises a sequence having at least 92% sequence identity to SEQ ID NO: 1. In some embodiments, the exogenous nucleic acid comprises a sequence having at least 93% sequence identity to SEQ ID NO: 1. In some embodiments, the exogenous nucleic acid comprises a sequence having at least 94% sequence identity to SEQ ID NO: 1. In some embodiments, the exogenous nucleic acid comprises a sequence having at least 95% sequence identity to SEQ ID NO: 1. In some embodiments, the exogenous nucleic acid comprises a sequence having at least 96% sequence identity to SEQ ID NO: 1. In some embodiments, the exogenous nucleic acid comprises a sequence having at least 97% sequence identity to SEQ ID NO: 1. In some embodiments, the exogenous nucleic acid comprises a sequence having at least 98% sequence identity to SEQ ID NO: 1. In some embodiments, the exogenous nucleic acid comprises a sequence having at least 99% sequence identity to SEQ ID NO: 1. In some embodiments, the exogenous nucleic acid comprises the sequence of SEQ ID NO: 1.

In some embodiments, the exogenous PRL-1 gene or homolog thereof encodes a polypeptide comprising an amino acid sequence having at least about 90% sequence identity to SEQ ID NO: 2. In some embodiments, the exogenous PRL-1 gene or homolog thereof encodes a polypeptide comprising an amino acid sequence having at least about 91% sequence identity to SEQ ID NO: 2. In some embodiments, the exogenous PRL-1 gene or homolog thereof encodes a polypeptide comprising an amino acid sequence having at least about 93% sequence identity to SEQ ID NO: 2. In some embodiments, the exogenous PRL-1 gene or homolog thereof encodes a polypeptide comprising an amino acid sequence having at least about 94% sequence identity to SEQ ID NO: 2. In some embodiments, the exogenous PRL-1 gene or homolog thereof encodes a polypeptide comprising an amino acid sequence having at least about 94% sequence identity to SEQ ID NO: 2. In some embodiments, the exogenous PRL-1 gene or homolog thereof encodes a polypeptide comprising an amino acid sequence having at least about 95% sequence identity to SEQ ID NO: 2. In some embodiments, the exogenous PRL-1 gene or homolog thereof encodes a polypeptide comprising an amino acid sequence having at least about 96% sequence identity to SEQ ID NO: 2. In some embodiments, the exogenous PRL-1 gene or homolog thereof encodes a polypeptide comprising an amino acid sequence having at least about 97% sequence identity to SEQ ID NO: 2. In some embodiments, the exogenous PRL-1 gene or homolog thereof encodes a polypeptide comprising an amino acid sequence having at least about 98% sequence identity to SEQ ID NO: 2. In some embodiments, the exogenous PRL-1 gene or homolog thereof encodes a polypeptide comprising an amino acid sequence having at least about 99% sequence identity to SEQ ID NO: 2. In some embodiments, the exogenous PRL-1 gene or homolog thereof encodes a polypeptide comprising an amino acid sequence set forth by SEQ ID NO: 2.

In some embodiments of the disclosure, the PRL-1 gene in the exogenous nucleic acid is operably linked to a heterologous promoter. A coding nucleic acid sequence is "operably linked" to a regulatory sequence (e.g., promoter) if the regulatory sequence is capable of exerting a regulatory effect on the coding sequence to which it is linked.

In some embodiments, the heterologous promoter is a constitutive promoter. In some embodiments, the heterologous promoter is a tissue specific promoter. In some embodiments, the heterologous promoter is a plant promoter. In some embodiments, the promoter is a tissue specific promoter. Examples of promoters suitable for use are provided above in this disclosure.

In some embodiments, the exogenous nucleic acid is stably transfected or transformed into the plant genome. In stable transformation, the exogenous polynucleotide is integrated into the plant genome and as such it represents a stable and inherited trait.

In some embodiments, the genetically modified plant, plant cell or plant tissue is selected from the group consisting of genera Acer, Afzelia, *Allium, Arabidopsis, Agrostis, Avena, Betula, Brassica, Capsicum, Citrullus, Cucumis, Eucalyptus, Fagus, Festuca, Fraxinus*, Fragaria, Glycine, *Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

EXAMPLES

The steps of the method described in the various examples disclosed herein are sufficient to carry out the methods of the present disclosure. Thus, in an example, a method consists essentially of a combination of the steps of the methods disclosed herein. In another example, a method consists of such steps.

The following examples are presented to illustrate the present disclosure. The examples are not intended to be limiting in any manner.

Example 1: PRL-1, Potri.012G062600, has Unique Nucleotide Sequences Absent in any Other Plants Variation in non-photochemical quenching (NPQ) induction and relaxation parameters were assessed across the GWAS population in Corvallis, Oregon. After running association mapping for NPQ parameters, a notable 54.5 kb region encompassing SNPs from positions Chr12: 7204090 to Chr12: 7258590 was associated with slow and medium relaxing NPQ Aq3 (p=2.64E-36), Aq2 (p-4.52E-30), and τq2 (p=1.08E-28). This interval contained an orphan gene annotated as a RIBULOSE BISPHOSPHATE CARBOXYLASE/OXYGENASE LARGE SUBUNIT-RELATED (Potri.012G062600), or PRL-1.

PRL-1 has three exons, among which the first two are unique to *P. trichocarpa* (FIG. 1A). Amino acid sequence-based blast search indicated the closest sequence matching the first exon corresponds to *Streptomyces* sp., a *Populus* endophyte, coding for a glycosyltransferase family protein. The second exon had a match to a DNA-binding protein D-ETS–6 from Trachymyrmex *septentrionalis*, an ant that grows a subterranean fungus known to colonize *Populus*. These two species of endophytes and colonizers have been associated with different *Populus* species, including *P. deltoides, P. tremuloides*, and *P. trichocarpa*, however, the integrated sequence seems to be *P. trichocarpa*-specific, not found in any other sequenced *Populus* genomes. The third exon is a conserved rbcL sequence ⅓ length from the C-terminus (FIG. 1A). PRL-1 protein modeling indicates a helix-extended-helix motif, with alpha structure at the N-terminus, due to the two acquired exons (FIG. 1B).

Figure 1D:
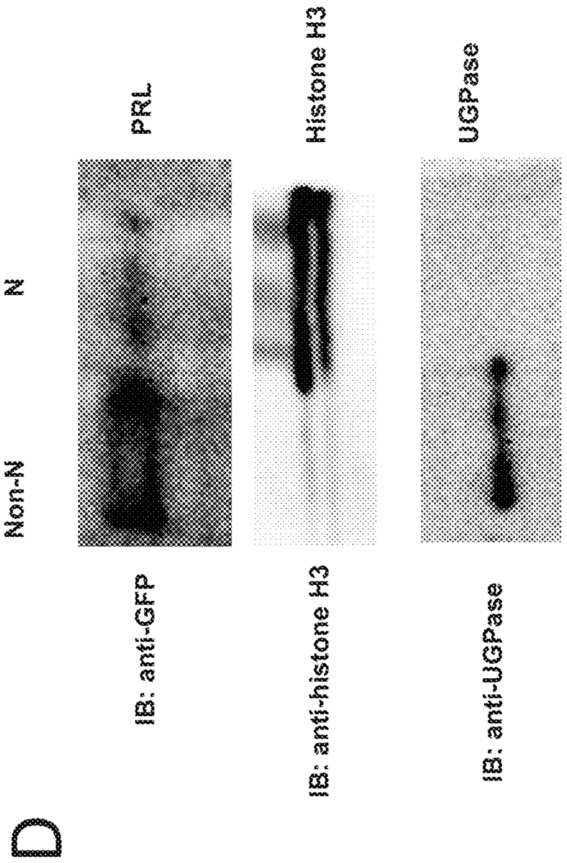
Figure 2:
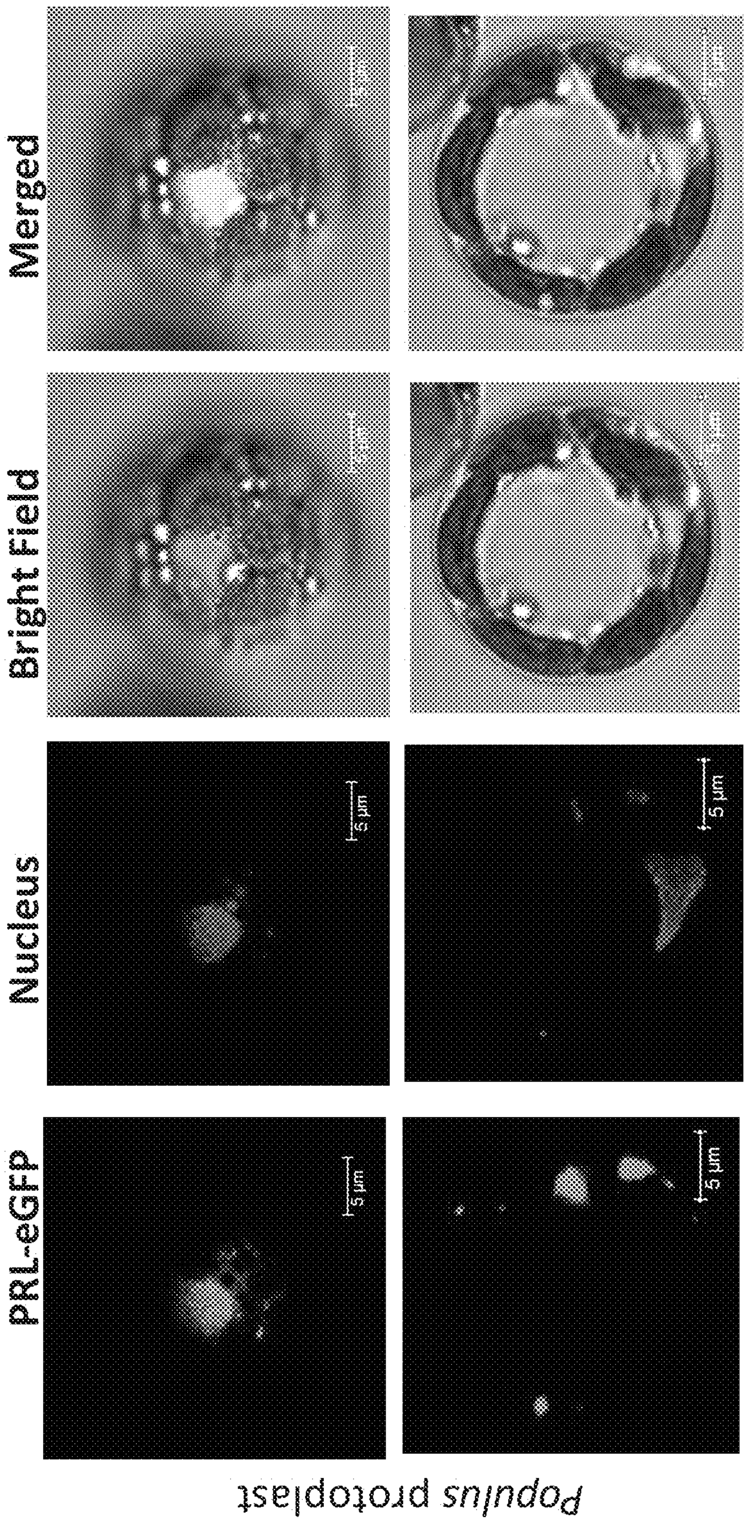
FIG. 2 In vitro subcellular localization of PRL-1 in *Populus* protoplast. *Populus* protoplasts infiltrated with PRL-1-eGFP while nucleus is stained with fluorescent dye propidium iodide.

Example 2: PRL-1 Accumulates in the Nucleus, Plastid, and Endoplasmic Reticulum A C-terminal GFP fusion with PRL-1 (PRL-1-eGFP) was created to determine the protein subcellular localization. Following agroinfiltration in *N. benthamiana*, PRL-1-eGFP localized to the plastid, nucleus, and endoplasmic reticulum (ER) (FIG. 1C). Similarly, *Populus* (FIG. 2) protoplasts transfected with PRL-1-eGFP showed nuclear and non-nuclear (chloroplast) localization. Additionally, PRL-1-eGFP was expressed in *Populus* protoplast and cell fractionation analysis performed followed by immunoblotting (FIG. 1D). The cell fractionation partitioned cellular components into nuclear and non-nuclear parts validated by the nuclear (Histone H3) and non-nuclear (UGPase) markers. The anti-GFP antibody detected the presence of PRL-1 in both nuclear and non-nuclear fractions, confirming the subcellular localization noted above (FIG. 1D). Hence, it was concluded from in vitro *Populus* protoplasts, in vivo *N. benthamiana* systems, and cell fractionation analysis that PRL-1 is localized in the nucleus and plastid. The observed nuclear localization of PRL-1 could be attributed to the uniquely acquired exons at the N-terminus with helix-extended-helix motif and predicted DNA binding activity, discussed in the next section. Moreover, having one-third of the canonical rbcL sequence (FIG. 1A) and the plastid localization suggests that PRL-1 may have photosynthesis-related function. ER has been reported as a port of protein entry to membrane-bound organelles by properly folding, assembling, and modifying a newly synthesized protein. The observed PRL-1 localization to the ER suggests PRL-1 proofreading and proper packaging prior to accumulation in the nucleus and plastid, together suggesting a putative transcriptional and photosynthesis-related roles.

Example 3: PRL-1 has a Transcriptional Repressor Activity and Interacts with Photosynthesis Regulatory Proteins With the predicted DNA binding motif at the N-terminus, and demonstrated nuclear and plastid localization, gene expression regulatory activity is suspected. Therefore, it was investigated if PRL-1 has transcriptional activator and/or repressor activity using the *Populus* protoplast transient expression system. Constructs of PRL-1 fused with Ga14-DNA binding domain (GD-PRL-1) were made along with two reporter constructs for transcriptional activator and repressor assay. Results indicated that PRL-1 has no transcriptional activator activity but does have repressor activity (FIG. 3A, B).

Figure 3E:
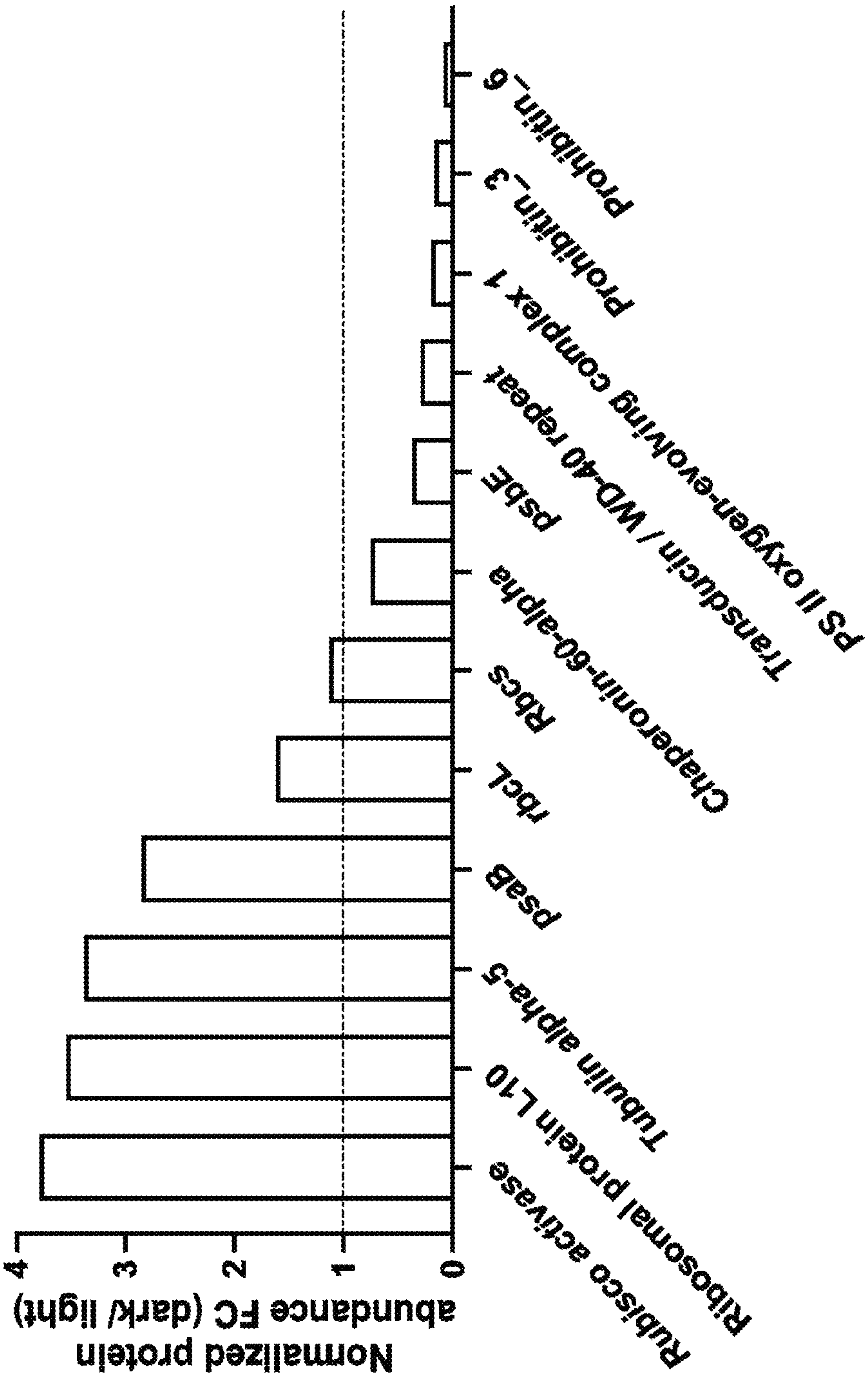

Given the observed transcriptional activity, the presence of PRL-1 interacting proteins were searched for through immunoprecipitation-based mass spectrometry (IPMS) (FIG. 3C). Leaves of PRL-1-eGFP and Wild-type *Arabidopsis* plants were collected following exposure to high light (2000 μmol $S^{-1}$ $m^{-2}$) and dark conditions. PRL-1 interacting proteins were captured by GFP-coated magnetic beads and identified using IPMS. The absence of proteins from the 'wash buffer' before elution or uncomparably trace amount in wild-type indicated lack of non-specific protein recovery (FIG. 3C). 379 and 429 proteins from high light and dark conditions were identified, respectively, among which 307 of the proteins were shared with differences in abundance (FIG. 3D). Since the complete protein complex interacting with PRL-1 was pulled down, the identified proteins could be from direct or indirect interactions. Gene ontology-based analysis of the identified proteins showed significant enrichment of plastid inner membrane, chloroplast inner membrane, proteasome regulatory particle base subcomplex, and small ribosomal subunit cellular components accompanied by respective biological processes. Rubisco activase, a regulator of Rubisco enzyme activity, exhibited almost 4-fold abundance in the dark versus light. Similarly, large and small subunits of Rubisco (rbcL and rbcS) and ribosomal protein L10 were co-precipitated more in the dark (FIG. 3E). On the other hand, secondary metabolite regulating prohibitin (prohibitin 3 and 6) and transducin WD40 repeat transcription factor along with PSII oxygen-evolving complex 1, were prevalent under high light conditions (FIG. 3E). The dynamic accumulation of these proteins as a direct/indirect interacting partners of PRL-1 in a light-dependent manner suggested a PRL-1 regulatory mechanism related to enhanced photosynthetic efficiency, discussed in the following sections.

Example 4: Environmental Adaptation May have Impacted PRL-1 Occurrence and Expression Differential gene expression is crucial for stress tolerance or evolutionary adaptation, especially for sessile organisms such as plants. Combining the expression levels of PRL-1 across the GWAS population (FIG. 4) with long-term endemic site climate data, it was found that geographic temperature and moisture levels of the original GWAS genets significantly contributed to variations in PRL-1 expression levels, such that, Mean Annual Temperature (p=0.00887),Degree-Days below 00C (chilling degree-days) (p=0.00287), Number of Frost-Free Days (p=0.03305), and Hargraves Climatic Moisture Deficit (p=0.01032) was associated significant differences in PRL-1 expression levels. Genotypes that showed the highest expression of PRL-1 originated from the coastal regions with high mean annual precipitation, low Hargreaves climatic moisture deficit, and lower altitudes.

Example 5: PRL-1 is Associated with Improved Biomass Accumulation in *Populus trichocarpa* and *Arabidopsis thaliana*

Figure 4:
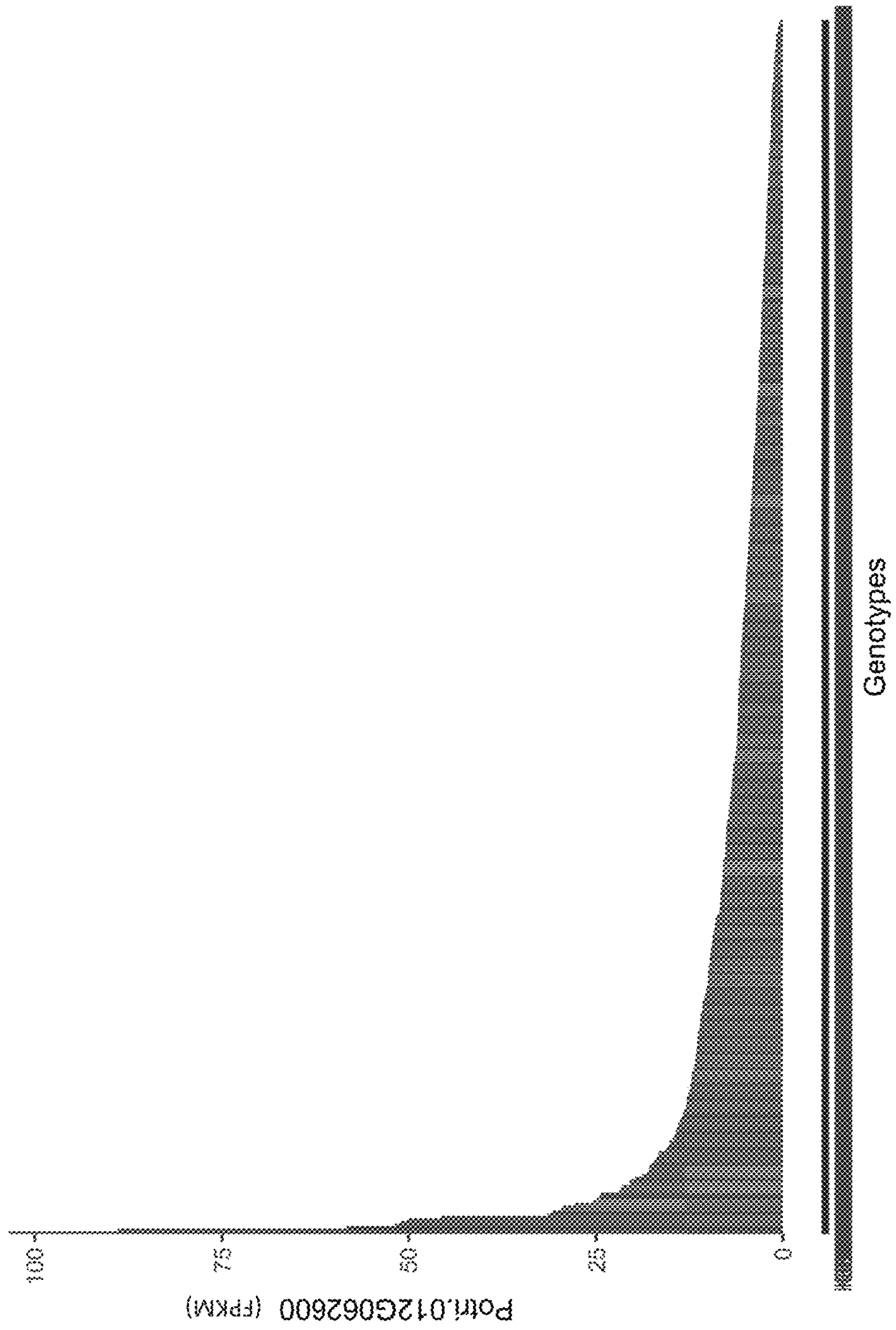
FIG. 4 Expression levels of PRL-1 (Potri.012G062600) across the GWAS population.
Figure 5A:
Figure 6A:
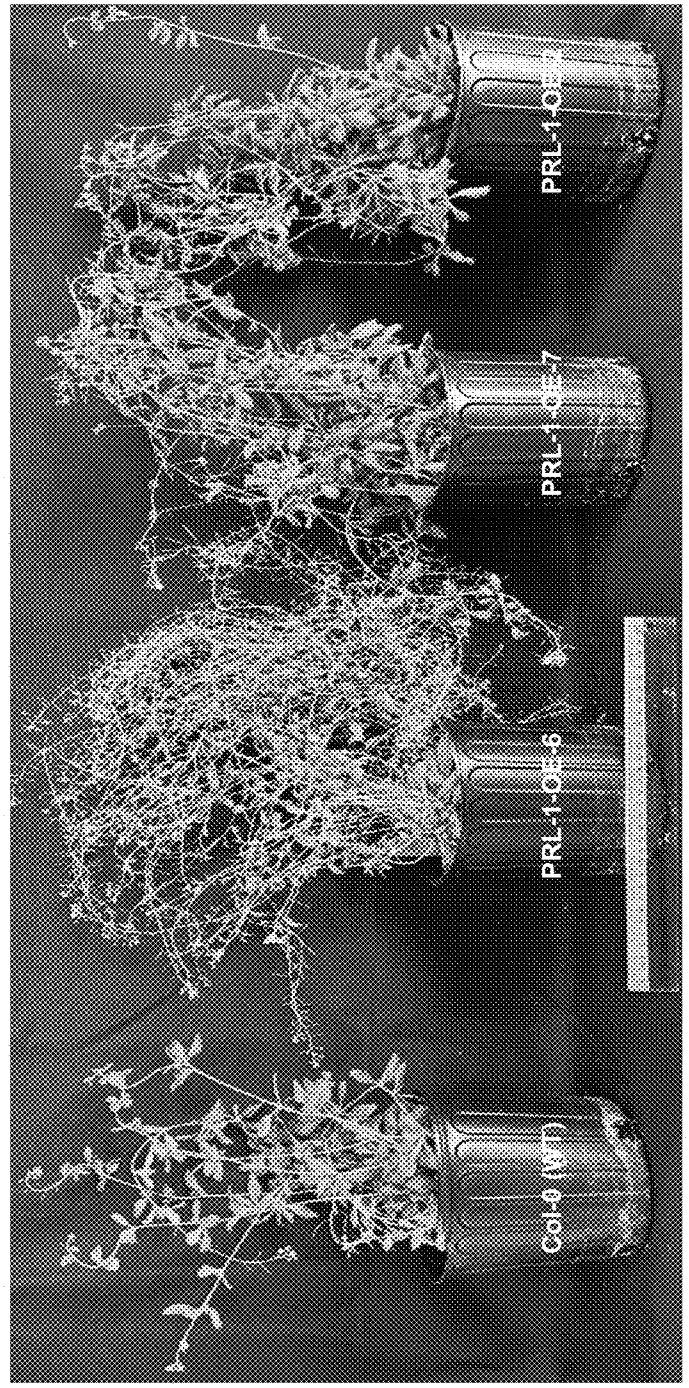
Figure 6E:
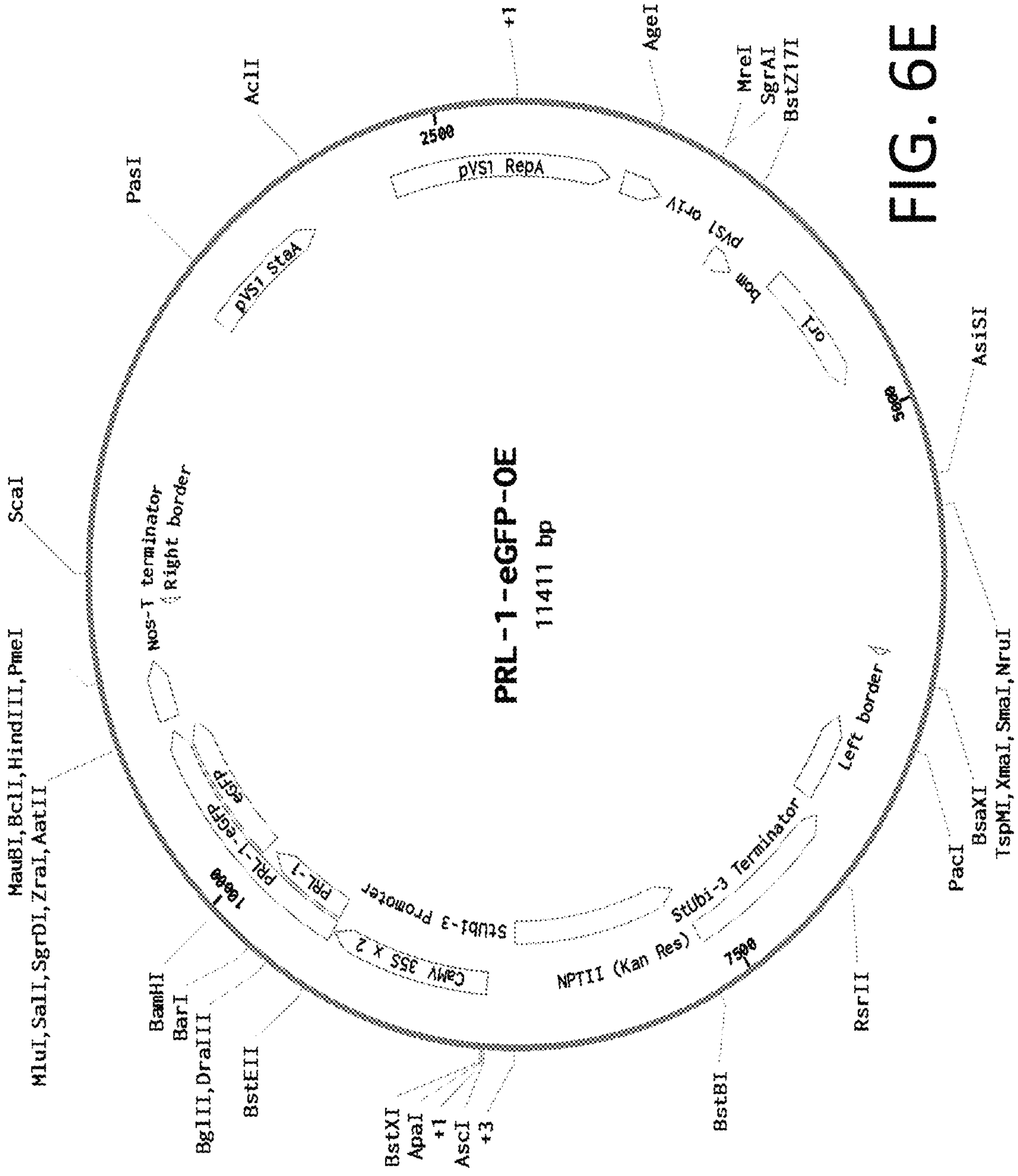
Figure 6F:
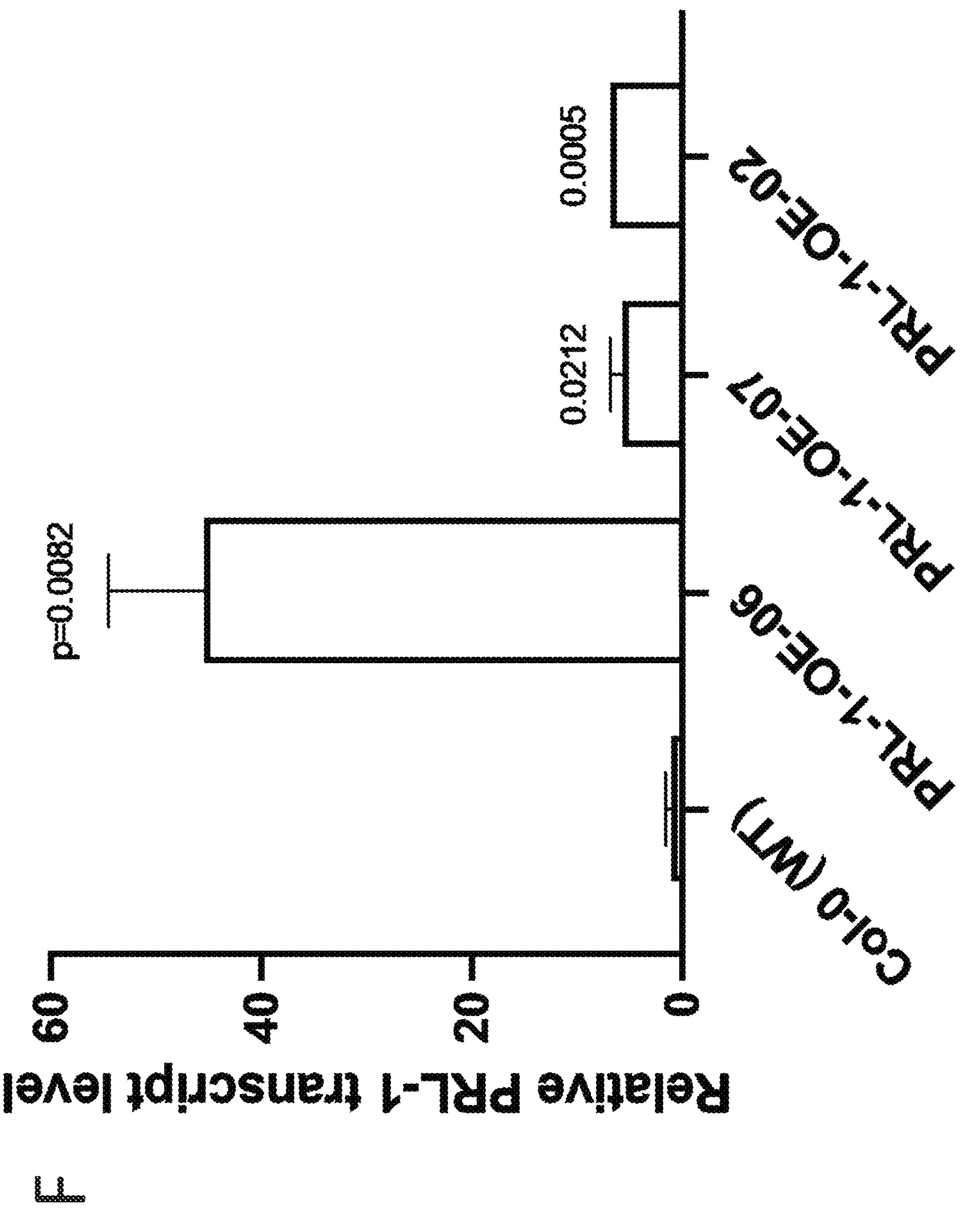

With the observed transcriptional activity, subcellular localizations of PRL-1 and interaction with Rubisco regulatory elements, its physiological impact was investigated. In the GWAS panel, expression levels of PRL-1 in FPKM (Fragments Per Kilobase of transcript per Million mapped reads) ranges from 103 to 0.43 (FIG. 4). Of these, studies focused on genotypes from both extremes with the top 20 highest expressors of PRL-1 labeled as 'HEP' (High Expressors of PRL-1) and lowest 20 expressors of PRL-1 labeled 'LEP' (Low Expressors of PRL-1). For example, HEP genotype KTMA-12-4, showed enhanced biomass accumulation after growing in the greenhouse for six months while the low expressor HARA-26-2 showed a shorter and bushy phenotype (FIG. 5A,B). HEP genotypes grown in a common garden at Placerville, CA showed plant height of 17 to 35% higher than LEP over four years and 88% greater stem volume (FIG. 5C, D). Similarly, 13-year-old (2009 to 2022) HEP genotypes growing in a common garden at Clatskanie, Oregon showed a 37% increase in stem diameter relative to LEP genotypes (FIG. 5E). Similarly, field-grown HEP genotypes at Placerville common garden showed 38% more crown area (FIG. 5F). Similar observations were made at the UC-Davis common garden, where HEP genotypes had significantly more stem diameter compared to LEP genotypes after three years of growth (FIG. 5G).

To determine if the observed greenhouse and field biomass gains in HEP accessions is mainly contributed by PRL-1, PRL-1 was heterologously expressed in *Arabidopsis* (FIG. 6A-F). A significant (p=0.01) increase in biomass (FIG. 6B, C) and higher (p-0.01) seed yield (FIG. 6D was observed in the heterologous PRL-1 expressed *Arabidopsis.*

Figure 7:
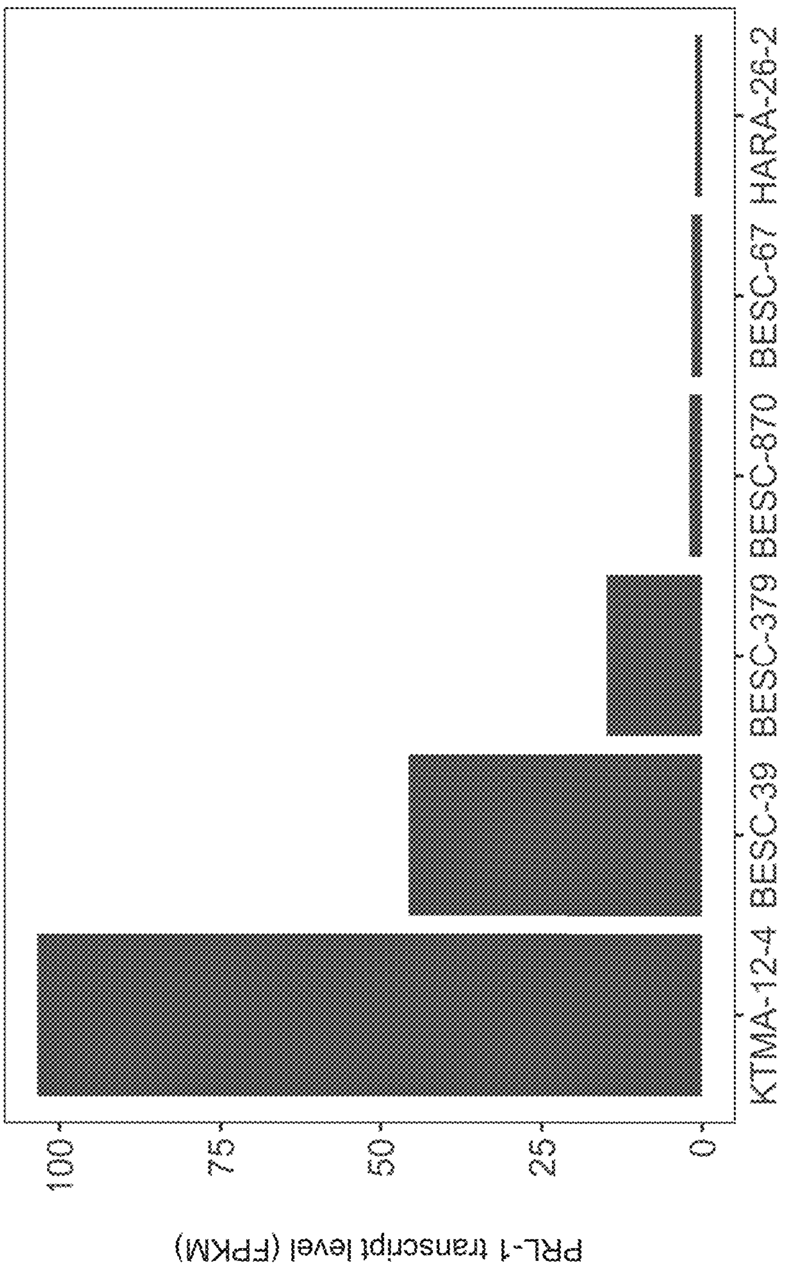
FIG. 7 Expression levels of PRL-1 in selected HEP and LEP genotypes used for NPQ measurement.
Figure 8A:
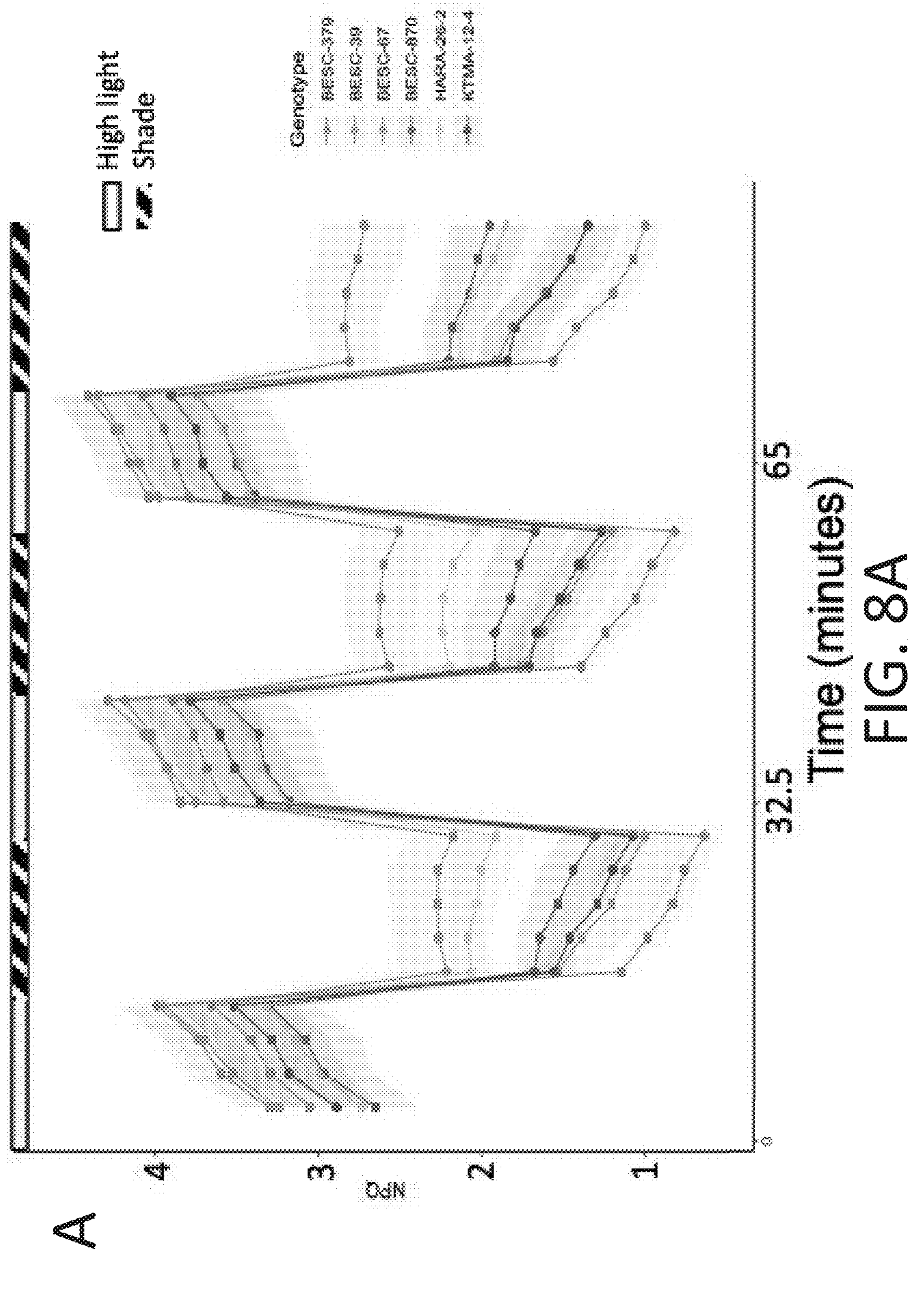
Figure 8B:
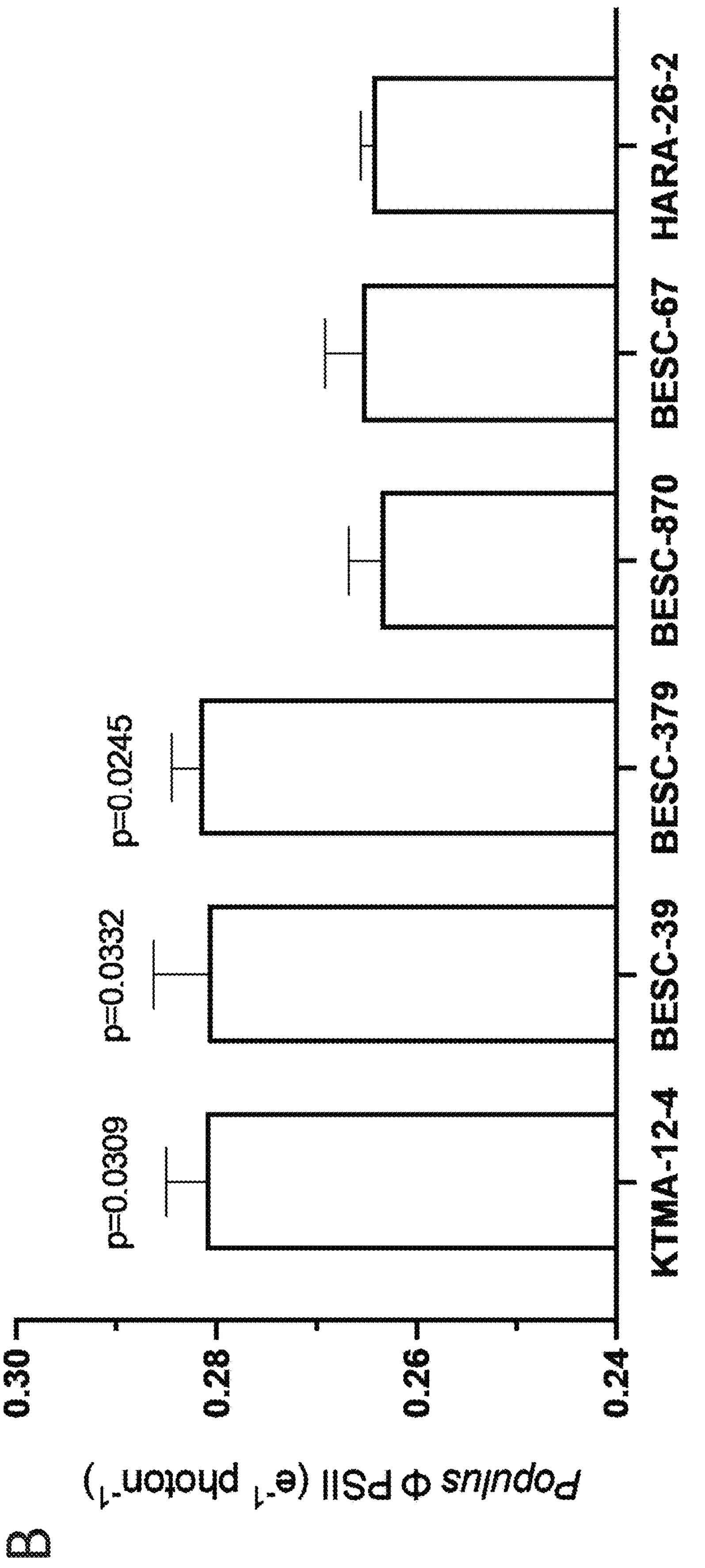
Figure 8C:
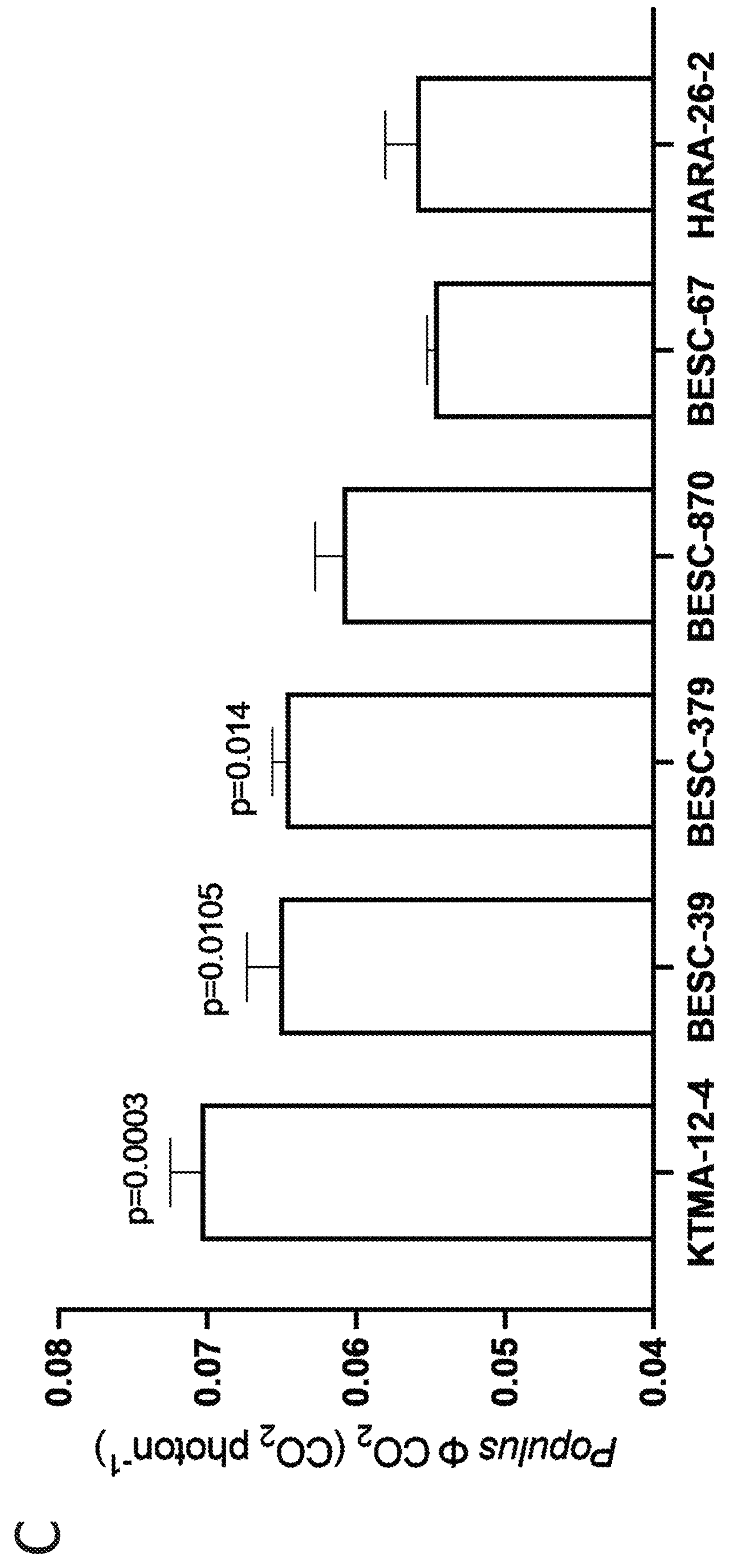
Figure 8D:
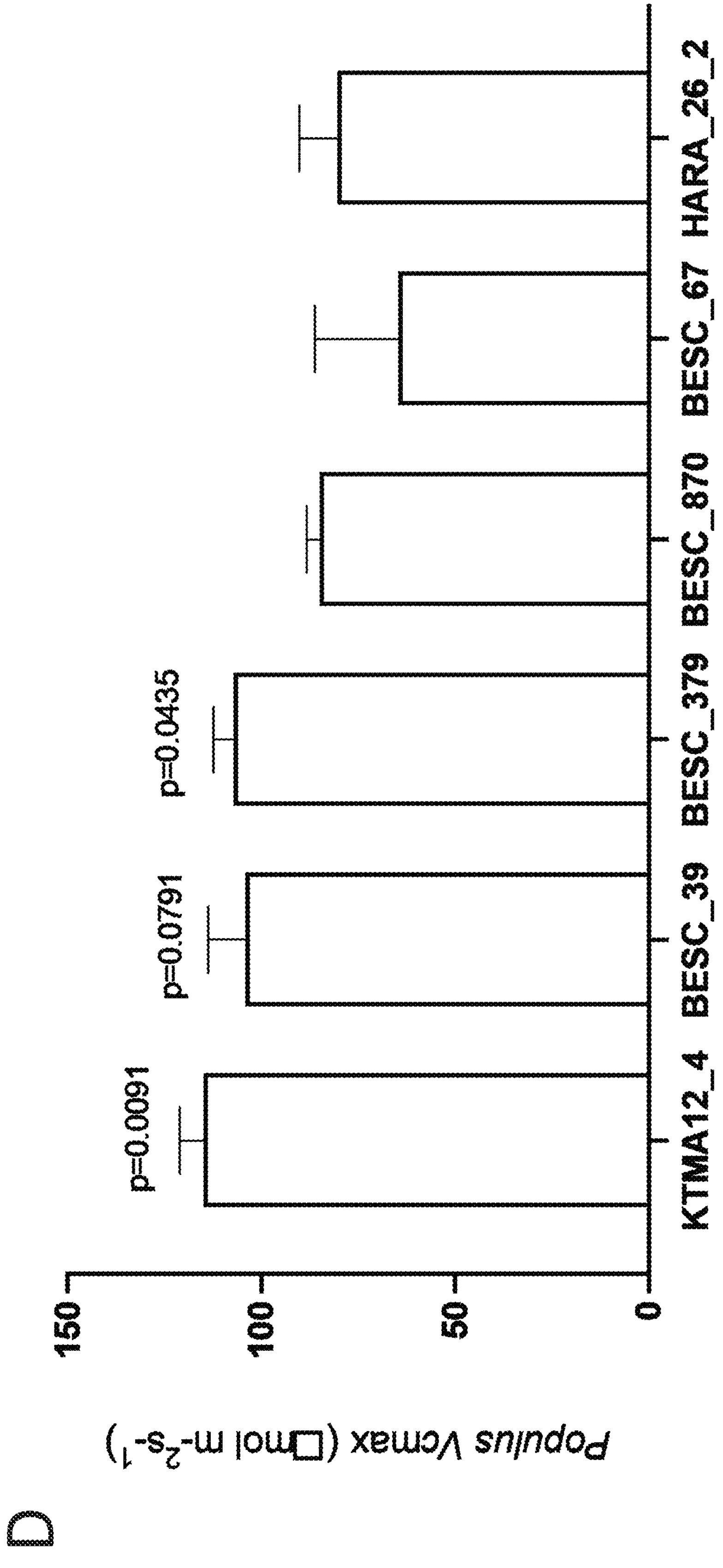
Figure 8E:
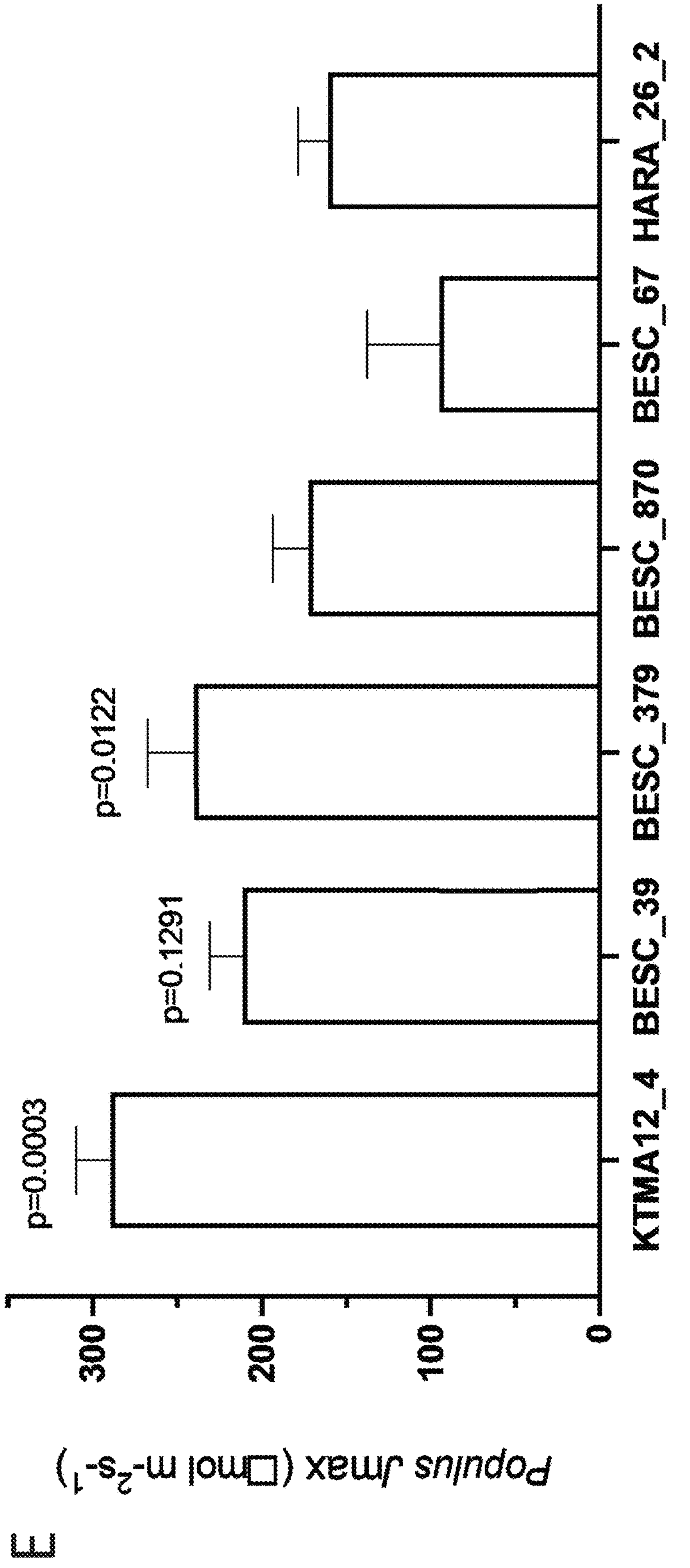

Example 6: PRL-1 Improve Non-Photochemical Quenching (NPQ) Response and Photosynthetic Efficiency Under Fluctuating Light Three genotypes from high expressors of PRL-1: KTMA-12-4 (103.4 FPKM), BESC-39 (45.7 FPKM), and BESC-379 (14.8 FPKM), and three genotypes from low expressors of PRL-1: BESC-870 (2.0 FPKM), BESC-67 (1.6 FPKM), and HARA-26-2 (1.1 FPKM) were selected for comparison in order to investigate the physiological mechanisms underlying increased biomass gain in HEP genotypes (FIG. 7). HEP and LEP genotypes were exposed to high light and low light episodes to determine NPQ induction upon high light exposure and its relaxation following a transition to low light. HEP genotypes triggered NPQ quicker and maintained higher NPQ upon exposure to high light intensities (FIG. 8A). HEP genotypes BESC-379 and BESC-39 had the highest NPQ values during high light, whereas LEP BESC-870 and HARA-26-2 possess the lowest levels of NPQ values during episodes of high light (FIG. 8A). Interestingly, HEP genotypes tend to relax NPQ more rapidly and to lower levels (FIG. 8A), whereas LEP genotypes, such as BESC-870, tended to dissipate NPQ slower and maintain higher levels. When photosynthesis is light-limited, higher levels of NPQ decrease the amount of absorbed light energy available to $CO_2$ assimilation, negatively impacting plant growth and performance. Accordingly, better quantum efficiency of $CO_2$ assimilation (Φ $CO_2$) and quantum efficiency of linear electron transport (Φ PSII) was observed in HEP genotypes (FIG. 8B, C). In addition, differences in steady state photosynthesis between HEP and LEP genotypes were investigated. A significantly higher Vcmax and Jmax values in HEP *P. trichocarpa* genotypes were observed (FIG. 8D, E).

Dynamic NPQ responses to different light regimes combined with photosystem efficiency could explain why high PRL-1 expressors tend to have higher biomass accumulation demonstrated in FIG. 5A-G. In line with this observation, transgenic *Arabidopsis* with increased expression levels of PRL-1 showed enhanced Φ $CO_2$ and Φ PSII (FIG. 8F,G), combined with a significantly higher Vcmax and Jmax values (FIG. 8H,I). This may explain the higher biomass accumulation (FIG. 6B,C) and greater seed yield (FIG. 6D).

As such, it was demonstrated that PRL-1 accumulates in the nucleus, plastid, and endoplasmic reticulum, orchestrating improved photosynthesis efficiency in both *P. trichocarpa* and *Arabidopsis*. The observed interaction of PRL-1 with Rubisco subunits and regulatory elements, such as rbcL and rbcS, along with Rubisco activase, in a light-dependent manner suggests a possible improvement strategy to enhance photosynthetic efficiency. PRL-1-mediated enhanced photosynthesis efficiency was seen from plants grown in the growth chamber, greenhouse, and fields that spanned up to 13 years in three different locations. *Populus* plants with increased expression levels of PRL-1 performed better under fluctuating light conditions via improved NPQ relaxation and induction. HEP genotypes possessed a rewarding strategy by displaying rapid NPQ adaption, while LEPs were more conserved in their response to fluctuating light levels, maintained intermediate NPQ, and reduced photosynthesis efficiency. Transgenic *Arabidopsis* plants heterologously expressing PRL-1 had similar higher photosystem efficiency, increased biomass, and improved seed yield.

General Methods

Propagation of *Populus* Stem Cuttings for Greenhouse Experiments

Stem cuttings were collected from three-year-old *Populus* trees at Clatskanie, Oregon, field site during the dormant growth stage (Winter 2021). Stem cuttings were propagated with at least three nodal cuttings, treated with 0.1% Zerotol fungicide, dipped in rooting hormone, and planted in perlite media. Cuttings were kept under mist until roots and leaves were fully developed. Fully developed cuttings were transferred into soil pots, and phenotypic measurements, such as plant height were recorded at six-months post-transplantation into the soil.

*Populus* GWAS Population Panel and Phenotypic Measurements

The *Populus* GWAS mapping panel was collected across the latitudinal range of the species (38.8° to 54.3° N) in the Pacific Northwest region of North America. From this collection, 1,100 unrelated genotypes were established in Corvallis (44°35'17"N; 123°11'36"W) Oregon in 2008 with three replicates. The site soil type is classified as Fluventic Haploxerolls with 60% sand, 26% silt, 14% clay, and 3.5% organic matter. Subsets of the population were planted at UC-Davis, CA and Placerville, CA. Phenotypic measurements were collected from High and Low Expressers of Potri.012G062600 (HEP and LEP) growing at Clatskanie, Oregon, UC-Davis, CA and Placerville, CA. Diameter at Breast Height (DBH) from 13 years-old *Populus* trees growing at Clatskanie field site were collected in December 2022. Plant height data were collected at UC-Davis, CA for the years of 2008 to 2012. *Populus* stem volume and crown area were recorded from trees growing at Placerville, CA.

Genome-Wide Association Analysis

Whole-genome resequencing, SNP/InDel calling, and SnpEff analysis for the 545 individuals of this *Populus* GWAS population were previously described. An addition of 372 genotypes were incorporated in this study. A total of 8,301,860 SNP/InDels with minor allele frequencies≥0.05 were used for kinship relatedness matrix estimation for correction of genetic background effect using Genome-wide Efficient Mixed Model Association (GEMMA). The Bonferroni significance threshold for multiple testing was used to declared SNP-Trait associations.

Growing *Arabidopsis* for Physiological Performance and Yield Determination

Seeds of transgenic and Col-0 wild type plants were first treated with 70% ethanol for two minutes followed by 50% bleach (5% active chlorine) for 10 minutes, with occasional shaking. Seeds are then thoroughly rinsed three time with sterile distilled water, plated on ½ MS semi-solid media, stratified at 4° C. in a dark for three days, and transferred to germinator chamber (Nor-Lake Scientific NSLC331WSW/0GMH) for a week. The growth chamber is set to 23° C., 65% relative humidity and light intensity of 50 µmol. The MS media used for transgenic plants were fortified with 50 µM Kanamycin sulfate (Sigma, CAS 25389-94-0) as a selective marker. Germinated *Arabidopsis* seeds were transferred to soil (Sungro Metro-Mix 830-F3B RSi) and grown in a plant growth room chambers (Conviron, BDW80) set to 23° C., 65% relative humidity, and light intensity of 130 µmol (Growlite FPV24-A). T1 transgenic and Col-0 wild-type *Arabidopsis* plants were grown in IL pots under short day (8:16) in a completely randomized design to conveniently perform light fluctuation experiment using LI-6800 (LI-COR Biosciences. USA).

To determine seed yield and biomass, T1 generation transgenic and wild type (Col-0) *Arabidopsis* plants were grown in a completely randomized design in 0.5L soil containers in a long day (16/8) or short day (8/16) for 10 weeks, till the plants senesce. Seeds were collected per plant bases and biomass was let to dry overnight at 65° C. to determine dry biomass yield.

Chlorophyll Fluorescence Analysis from GWAS *Populus* Population

Chlorophyll fluorescence analysis was performed and NPQ relaxation kinetics calculated for leaf disks collected from mature leaves of Poplar. Briefly, three 4.8 mm leaf disks were collected from the upper-most mature leaf of each replicate strip in the field using a cork borer (Humboldt H9663; Fisher Scientific 07-865-10B). Leaf disks were floated on $dH_2O$ in a 24-well plate which was sealed with parafilm for transportation back to the laboratory. Leaf disks were then transferred to a square petri dish lined with wet filter paper, and plates sealed with parafilm and wrapped in aluminum foil for overnight incubation to allow for relaxation of long-term NPQ. Overnight incubated disks were subjected to 10 min illumination at 1000 µmol $m^{-2}$ $s^{-1}$ white light (6500 K) followed by 50 min of darkness. $F_m$, was determined by applying saturating pulses (4000 µmol $m^{-2}$ $s^{-1}$ white light) at 9, 40, 60, 80, 100, 120, 160, 200, 240, 300, 360, 420, 480, 540, and 598s after the actinic light was turned on, and at 1, 2, 4, 6, 8, 10, 14, 18, 22, 26, 32, 38, 44, and 50 min after the actinic light was turned off. The background was excluded automatically and NPQ values at each pulse were calculated. NPQ values for each disk were normalized by dividing the NPQ at each timepoint by that disc's maximum NPQ. NPQ parameters Aq1, Aq2, and Aq3 (the proportion of maximum NPQ from fast, medium and slow relaxing NPQ respectively), and τqE and τqM (the half-life of relaxation of Aq1 and Aq2 respectively) for each disc were then calculated by fitting a double exponential function to the last 15 normalized NPQ values (the last point taken in the light and all subsequent points), with Equation 1:

$$NPQ = Aq3 + Aq1^{\left(-\frac{t}{\tau q1}\right)} + Aq2^{\left(-\frac{t}{\tau q2}\right)} \quad \text{Equation 1}$$

using custom R scripts.

Photosynthetic Efficiency Parameters and NPQ Values Under Fluctuating Light 94

The quantum efficiency of $CO_2$ assimilation ($CO_2$) and quantum efficiency of linear electron transport (Φ PSII) parameters of photosynthetic efficiency were calculated by obtaining $CO_2$ assimilation response curve to fluctuating light. In brief, $CO_2$ assimilation responses were obtained on one-month-old fully expanded *Arabidopsis* and *Populus* leaves, 6th from the top in *Populus*, using LI-6800 fitted with a Multiphase Flash Fluorometer (6800-01A) and cuvette size (LI-COR Biosciences. USA). LI-6800 was set to a $CO_2$ level of 1500 μmol mol-1 with a light source of 1500 μmol $m^{-2}$ $s^{-1}$ comprising 1350 μmol $m^{-2}$ $s^{-1}$ red light (90%) and 150 μmol $m^{-2}$ $s^{-1}$ (10%) blue light. First, *Populus* plants were dark-adapted for 45 minutes prior to measuring $F_o$ and $F_m$ to calculate the maximum quantum yield of PSII photochemistry $F_v/F_m$, followed by light adaptation at 2000 μmol $m^{-2}$ $s^{-1}$ PPFD for at least 20 minutes until reaching a steady state. Leaves were then subjected to a program of fluctuating light intensity with sequences of 2000, 1500, 2000, 1000, 2000, 800, 2000, 600, 2000, 400, 2000, 106 200, 2000, 170, 2000, 140, 2000, 110, 2000, 80, 2000, 50 μmol $m^{-2}$ $s^{-1}$ with a four-minute duration between each step. The average response values per light intensity was used to construct light response curves. Φ $CO_2$ was obtained by calculating the slope of $CO_2$ assimilation responses upon light fluctuation, while Q PSII used electron transport rates.

Non photochemical quenching, NPQ, was calculated from *Populus* leaf discs using Closed FluorCam FC 800-C (Photon Systems Instruments, Czech Republic) according to Gotarkar et al. In brief, nine leaf discs were collected using a cork borer (H-9663; Humboldt, USA) and placed with the adaxial side facing up on distilled water saturated Whatman filter papers. Leaf discs were dark-adapted for at least two hours before measuring chlorophyll fluorescence. The program used for chlorophyl fluorescence is provided in additional files. Dark adapted fluorescence ($F_o$) was measured over 2s and maximal fluorescence ($F_m$) was measured from 480 ms to 880 ms of a 960 ms pulse of saturating light (6500 μmol $m^{-2}$ $s^{-1}$).

To measure NPQ induction and relaxation, leaf discs were exposed to a period of 10 min high light followed by 20 min low light, repeated 3 times. High light was 2,000 μmol $m^{-2}s^{-1}$ 6500K light (set to 100% of maximum), and low light was 230 μmol $m^{-2}$ $s^{-1}$ 6500K light (set to 13.7% of maximum). $F_m$ was measured with saturating pulses 2.5, 5, 7.5, 10, 12.5, 15, 20, 25, and 30 min after the beginning of each of the three periods of high light, and NPQ at each of these timepoints was calculated by the FluorCam software.

Maximum Rate of Rubisco Carboxylase Activity and Photosynthetic Electron Transport One- and three-month-old *Arabidopsis* and *Populus* plants, respectively, were used to determine the maximum rate of rubisco carboxylase activity, Vcmax, and the maximum rate of photosynthetic electron transport (Jmax) at noon. Vcmax and Jmax values are calculated from A/Ci curves with LI-6800 fitted with a Multiphase Flash Fluorometer (6800-01A) and cuvette size of 6 $cm^2$ (LI-COR Biosciences, USA) reference levels of 400, 300, 200, 100, 50, 0, 400, 400, 600, 800, 1000, 1200 μmol $CO_2$ $mol^{-1}$. Light intensity, leaf temperature, fan speed, and flow rate were kept constant at 1500 μmol $m^{-2}$ $s^{-1}$ (1350 μmol $m^{-2}$ $s^{-1}$ red light (90%) and 150 μmol $m^{-2}$ $s^{-1}$ (10%) blue light), Txchg of 25° C., 10000 rpm, 500 μmol $s^{-1}$. Vcmax and Jmax were calculated using an r package, 'plantecophys' that analyze and model leaf gas exchange data.

PRL-1-eGFP Cloning and Generation of Transgenic *Arabidopsis* Plants

PRL (Potri.012G062600) with eGFP was amplified using a forward PRL-F (SEQ ID NO: 3): TCTATCTCTCTCGACCGCTATGGGTCACCA and reverse PRL-R (SEQ ID NO: 4):GAGACGTCGACGCGTAAGCTATTCGAGCTC primers. To amplify the backbone of p201N-Cas9 plasmid (Addgene plasmid #59175) devoid of the Cas9 for Gibson cloning, forward (SEQ ID NO: 5) CTTACGCGTCGACGTCTC and reverse (SEQ ID NO: 6) TAGCGGTCGAGAGAGATAGATT primers were used. PRL-eGFP was cloned into the p201N-Cas9 plasmid (Addgene plasmid #59175) backbone using Gibson assembly using the NEBuilder HiFi DNA assembly kit (New England Biolabs; #5520). Hence, PRL-eGFP driven by an enhanced 35S promoter with nopaline synthase termination sequence was created (FIG. 7A). The integrity of amplicons and final plasmid construct was verified by Sanger Sequencing (Eurofins Genomics) and used for subsequent transformation and localization studies. The binary vector was then transformed into Chemically competent *Agrobacterium tumefaciens* strain GV3101 (GoldBio; #CC-105). Wild-type (Col-0) *Arabidopsis thaliana* plants were transfected with PRL-eGFP binary vector by floral dip method (46). Positive *Arabidopsis* transformants were screened with selective marker (Kanamycin sulfate) containing ½ MS plates followed by PCR amplifications of PRL-1.

In Vivo Subcellular Localization Study

*N. benthamiana* leaves were co-infiltrated with PRL-1-eGFP in combination with a pCMU-152 NUCr nuclear-mCherry marker (Addgene; #61168), or plastid-mCherry marker (TAIR; #CD3-999), or Endoplasmic Reticulum (ER)-mCherry marker (TAIR; #CD3-960) to investigate the subcellular localization of PRL-1 in the nucleus, plastid, and endoplasmic reticulum, respectively. First, each plasmid was transformed into *Agrobacterium tumefaciens* GV3101 strain (GoldBio #CC-105) and co-infiltrated into one-month-old *N. benthamiana* leaves for in vivo localization study. Subcellular localization imaging was checked after 72 hours post-infiltration using Zeiss LSM 710 confocal microscope and images were processed using the Zeiss ZEN software package.

In Vitro Subcellular Localization Study

*Populus* and *Arabidopsis* protoplasts were isolated from leaf tissues using Cellulase Onozuka R-10 (Yakult Pharmaceutical Industry Co. Ltd, YAKL0012) and Macerozyme R-10 (Research Product International, M22010-5.0) according to Xie et al. 100 μl of protoplasts ($5\times10^6$) were transfected with 10 μg of PRL-1-eGFP binary vector using PEG-calcium transfection method and incubated under weak light for 14 hours for protein expression before imaging under Zeiss LSM 710 confocal microscope and images were processed using the Zeiss ZEN software package.

Cell Fractionation and Blotting of Protein Gels $5\times10^6$ of transfected *Populus* protoplast cells were prepared as described for the in vitro subcellular localization study. The transfected protoplasts were incubated for 14 hours under bench light for protein expression. Protoplast cells were then fractionated according to Xie et al. In brief, *P. trichocarpa* protoplast cells were collected following centrifugation at 2000 rpm for 10 minutes. Total protein from protoplast was extracted with extraction buffer (20 mM Tris-HCl, pH 7.4, 25% glycerol, 20 mM KCl, 2 mM EDTA, 2.5 mM MgCl2, 250 mM sucrose, 1 mM DTT, and 1 mM PMSF) incubation for 1 hour on ice. Subsequently, the cells were centrifuged at 1500 g (4° C.) for 10 minutes, collected the clear supernatant as a non-nuclear faction and precipitated with acetone. The non-nuclear fraction was treated with four times the sample volume pre-cooled to −20° C. acetone, vortexed, and incubated at −20° C. for one hour. The non-nuclear-acetone mixture was centrifuged at 15000 g at 4° C. for 10 minutes, decanted the supernatant without dislodging the pellet, and let the acetone evaporated from the pellet at room temperature for 30 minutes. The pellet was then used as a non-nuclear fraction for downstream analysis. In parallel, the nuclear fraction pellet was washed with nuclei resuspension Triton buffer (20 mM Tris-HCl, pH 7.4, 25% glycerol, 2.5 mM MgCl2, and 0.2% Triton X-100) with centrifugation in between at 1500 g (4° C.) for 10 min. The pellet was then washed with nuclei resuspension buffer (20 mM Tris-HCl, pH 7.4, 25% glycerol, and 2.5 mM MgCl2) and centrifuged at 1500 g (4° C.) for 10 min and kept the pellet as the nuclear fraction. The nuclear and non-nuclear pellets were resuspended in NuPAGE™ LDS Sample Buffer (4×) (NP0007), subjected to SDS-PAGE protein electrophoresis, and transferred into the PVDF membrane. Anti-Histone H3 (abcam, #ab1791) and anti-UGPase (Agrisera, #AS05 086) antibodies were used to verify the purity of the fractionated components of the *P. trichocarpa* protoplasts as nuclear and non-nuclear fractions, respectively. PVDF membrane was incubated with anti-GFP (enQuirebio, QAB10298) (1:1250), anti-histone (1:5000) (abcam, ab1791), and anti-UGPase (1:5000) (Agrisera, AS05 086) primary antibodies followed by anti-rabbit secondary antibody (Agrisera AS09 602; 1:10,000). The membrane was finally treated with ECL substrate (Promega Cat. #W1001) at room temperature and imaged using the Biorad ChemiDoc XRS+ imaging system.

Transactivation Assay

The transactivation assay in protoplasts was performed according to Xie et al. (47). 100 μl of 198 *Populus* protoplasts were transfected with ten micrograms of effector, reporter, and/or transactivator plasmids using the PEG-calcium transfection method. 100 ng of 35S: Luciferase 200 plasmid was co-transfected for each transfection as the internal control. Transfected protoplasts were incubated under darkness for 18 hours at room temperature. To measure GUS activity, protoplast lysates were incubated with 4-methylumbelliferyl b-D-glucuronide (MUG) at 37° C. 203 for 1h. Luciferase activity of protoplast lysates was measured using a Promega Luciferase Assay System (Promega, E1500) according to the manufacturer's manual. The fluorescence of 4-methylumbelliferone (4-MU) and luminescence were measured using Synergy Neo2 Hybrid multimode microplate reader (BioTek). GUS activity was normalized with luciferase activity. All transfections were performed in triplicate to calculate the mean value and SD, which were used in Student's t-tests.

RNA Extraction and qPCR 210

Total RNA was extracted combining CTAB and column-based Spectrum Total RNA kit (Sigma, STRNA50-1KT). Leaf samples were snap frozen in liquid nitrogen, grounded using SPEX SamplePrep GENO/GRINDER, and 100 mg leaves were used for RNA extraction. 840 μl of CTAB buffer (2% w/v CTAB, 100 mM Tris, 1.4M NaCl, 20 mM EDTA, 2% w/v PVP) with 10 μL of β-mercaptoethanol was added to leaf powder, vortexed for two minutes, and incubated at 56° C. with shaking (1800 rpm) for five minutes. 600 μL chloroform-isoamyl alcohol (24:1) was added, vortexed for 1 minute, and centrifuged for 8 minutes at maximum speed. The top layer is transferred into the Spectrum filtration column and centrifuged for one minute at full speed. The filtrate was mixed with 600 μL of 100% (v/v) ethanol and centrifuged in the Spectrum binding column for 1 minute. The column is washed with 300 μL of Wash Solution 1 and incubated with 79 μL on-column DNase I (Sigma #DNASE70-1SET) at room temperature for 15 minutes. The binding column was then washed with 500 μL of Wash Solution 1 and twice with Wash Solution 222 2. The column was incubated for 2 minutes with 30 μL of nuclease-free water, and total RNA was eluted after one-minute of centrifugation at full speed. The integrity and concentration of total RNA was determined using NanoDrop 2000 Spectrophotometer (Thermo Scientific). 1 μg of total RNA was added to synthesize cDNA using RevertAid Reverse Transcriptase kit (Thermoscientific; EP0441) with random hexamer. A 10 μL PCR reaction volume comprised of 227 5 μL Maxima SYBR Green/ROX qPCR master mix (thermoscientific; KO221), 0.6 μL 10 μM forward primer, 0.6 μL 10 μM reverse primer, 1 μL of cDNA (200 ng) and 2.8 μL water was used. PCR amplification used a thermocycling of 95° C. denaturation for 2 minutes followed by 35 cycles of 95° C. for 15 sec, 58° C. for 30 sec, and 72° C. for 60 secs for denaturing, annealing and extensions of the amplicon, respectively. qRT-PCR was performed using QuantStudio 6 Pro (Applied Biosystems) following primer efficiency check using a serial dilution of pulled samples. Elongation factor alpha and GAPDH were used as reference housekeeping genes. PRL-1 (Potri.012G062600) gene expression is calculated using the ddCq method from each plant with three technical replicates.

Genomic and plasmid DNA were extracted using DNeasy Plant Mini Kit (QIAGEN; 69104) and QIAprep Spin Miniprep Kit (QIAGEN; 27104), respectively, following user instructions. Amplicons from DNA were amplified using Phusion high-fidelity master mix with GC buffer (NEB, M0531L). PCR reactions from DNA samples used 98° C. denaturation temperature followed by 35 cycles of 98° C. for 30 sec, 58° C. for 30 sec, and 72-68° C. for 60 secs to 10 mins, 241 depending on product length in Mastercycler® *nexus* gradient thermal cycler (Eppendorf, 242 6331000025). Genomic DNA sequences for PRL were amplified using six pairs of primers:

```
Set1F (SEQ ID NO: 7):
CCATGTGTCATTACTGCGAAA,

Set1R (SEQ ID NO: 8):
TTTCTCGGGATTTACATTCTCC

Set2F (SEQ ID NO: 9):
CCGCTCTTATTCTCCGACAT,

Set2R (SEQ ID NO: 10):
TTACCCGGTACGAATCAA

Set3F (SEQ ID NO: 11):
GGAGGGATCGAAACCTTGAT,

Set3R (SEQ ID NO: 12):
TCTGTCATGACCCAGTCTCG

Set4F (SEQ ID NO: 13):
ACTCCAGCTATGGGTCACCA

Set4R (SEQ ID NO: 14):
AGGTGCGATTCACCTACCTG.

Set5F (SEQ ID NO: 15):
AGACGTGGTGCAACAACAAC

Set5R (SEQ ID NO: 16):
AGGAGTCGATGCAAGGTGAT
```

-continued

```
Set6F (SEQ ID NO: 17):
ATCACCTTGCATCGACTCCT

Set6R (SEQ ID NO: 18):
CAACATATCCATTGCTTGGAA
```

Immunoprecipitation and Mass Spectrometry

Immunoprecipitation-based isolation of PRL-1 direct/indirect interacting proteins were isolated according to previously published work (48) using a μMACS GFP isolation kit (Miltenyi Biotec, 130-091-125). In brief, eGFP-tagged *Arabidopsis* plants were exposed to 2000 μmol light intensity from sunlight for 10 minutes followed by 10 minutes in the dark. 100 mg leaf samples were collected at the end of each stage and snap-frozen in liquid nitrogen. The elute from the wash step, before final elution, was used as a negative control to check for the presence of unspecified protein binding to GFP magnetic beads. Subsequently, SDS-PAGE electrophoresis was done on the elutes using NuPAGE 4-12% 1.0 mm gels (Invitrogen, NP0321BOX) and silver stained prior to performing mass spectrometry.

For each sample elutes (20 μL), 5 μL of lysis buffer (20% sodium dodecyl sulfate) containing 10 mM diothiothreitol was added to denature proteins. Samples were vortexed and incubated for 10 minutes at 90° C. with constant shaking. The denatured protein sample was vortexed and centrifuged at 21,000×g for 10 minutes. Denatured proteins were alkylated with 30 mM iodoacetamide and incubated in the dark for 15 minutes to prevent the reformation of disulfide bonds. Sera-Mag beads were added (2 μL) and protein aggregation capture was performed. Acetonitrile (ACN) was added to each sample to reach a final concentration of 70%. Samples were vortexed, allowed to settle for 10 minutes, vortexed, and allowed to settle for a final 10 minutes. Tubes were placed on a magnetic rack and the supernatant was removed using a vacuum system. Samples were washed with 1 mL ACN and 1 mL 70% ethanol while on the magnetic rack. Samples were removed from the magnetic rack and beads were resuspended in 100 mM ammonium bicarbonate (ABC). Proteins were digested using two aliquots of sequencing grade trypsin (1 μg) overnight, followed by 3 h at 37° C. with constant shaking. The samples were placed on a magnetic rack and adjusted to 0.5% formic acid (FA). An AcroPrep Advance 96 well 10 KDa omega filter plate (Pall Corporation) was prepped by adding 100 μL of ABC to each 274 well and centrifuged at 1500×g for 10 minutes. Tryptic peptide samples were then arrayed in the filter plate and centrifuged at 1500×g for 30 minutes. Tryptic peptide flow through concentrations were assessed using the Nanodrop One spectrophotometer. Peptide mixtures were analyzed using one-dimensional liquid chromatography on an Ultimate 3000 RSLCnano system (Thermo-Fisher Scientific) coupled with a Q Exactive Plus mass spectrometer (Thermo-Fisher Scientific). For each sample, a 0.8-μg inject of each sample was flowed across an in-house-built reversed-phase (RP) C18 trap column (5 μm by 150 μm by 50 mm) using an aqueous solvent (5% ACN and 0.1% FA) for 10 min. The trapped peptides were separated by a 45-min linear organic gradient (250 nL/min flow rate) from 5% aqueous solvent (5% ACN and 0.1% FA) to 30% organic solvent (80% ACN and 0.1% FA) to separate peptides across an in-house-pulled nanospray analytical column (75 μm by 350 mm) packed with C18 Kinetex RP C18 resin (1.7 285 μm) (Phenomenex). All MS data were acquired with Thermo Xcalibur (version 4.2.47) using the top N method, where N could be up to 10. Target values for the full-scan MS spectra were 3×287 106 charges in the 300 to 1,500 m/z range with a maximum injection time of 25 ms. Transient times corresponding to a resolution of 70,000 at m/z 200 were chosen. A 1.6 m/z isolation window and fragmentation of precursor ions was performed by higher-energy C-trap dissociation with a normalized collision energy of 27 eV. MS/MS scans were performed at a resolution of 17,500 at m/z 200 with an ion target value of $1\times10^5$ and a 50-ms maximum injection time. Dynamic exclusion was set to 20s to avoid repeated sequencing of peptides. All MS raw data 293 files were analyzed using the Proteome Discoverer software (Thermo-Fisher Scientific, version 294 2.5). Each MS raw data file was processed by the SEQUEST HT database search algorithm and 295 confidence in peptide-to-spectrum (PSM) matching was evaluated by Percolator. Peptide 296 and PSMs were considered identified at $q<0.01$. Relative abundance of each protein was 297 calculated by dividing the summed total peptide abundance per protein by the total summed 298 abundances from each sample. 299

Statistical Analysis 300

R version 4.2.1 statistical environment was used to calculate statistical differences using a t-test 301 when comparing two groups, while ANOVA was performed in >2 groups followed by multiple 302 comparison tests.

What is claimed is:

1. A genetically modified plant, plant cell, or plant tissue, wherein the genetic modification comprises expression of an exogenous nucleic acid comprising a nucleotide sequence having at least 98% sequence identity to SEQ ID NO: 1 in the plant, plant cell, or plant tissue; and wherein the expression of the exogenous nucleic acid results in enhanced photosynthetic efficiency and/or plant biomass of the plant, plant cell, or plant tissue as compared to a wild-type plant, plant cell, or plant tissue without the genetic modification, wherein the plant is selected from *Arabidopsis* or *Populus*.

2. The genetically modified plant, plant cell, or plant tissue of claim 1, wherein the expression of the exogenous nucleic acid results in enhanced photosynthetic efficiency and/or plant biomass of the plant, plant cell, or plant tissue as compared to a wild-type plant, plant cell, or plant tissue without the genetic modification when exposed to a stable or a fluctuating light environment.

3. The genetically modified plant, plant cell, or plant tissue of claim 1, wherein the exogenous nucleic acid comprising a nucleotide sequence having at least 98% sequence identity to SEQ ID NO: 1 encodes a protein comprising an amino acid sequence having at least 98% sequence identity to SEQ ID NO: 2.

4. The plant, plant cell, or plant tissue of claim 1, wherein the exogenous nucleic acid comprising a nucleotide sequence having at least 98% sequence identity to SEQ ID NO: 1 is operably linked to a heterologous promoter.

5. The plant, plant cell, or plant tissue of claim 4, wherein the heterologous promoter is a constitutive promoter.

6. The plant, plant cell, or plant tissue of claim 4, wherein the heterologous promoter is a tissue-specific promoter.

7. The plant, plant cell, or plant tissue of claim 4, wherein the heterologous promoter is a *Populus trichocarpa* native promoter.

8. The genetically modified plant, plant cell, or plant tissue of claim 1, wherein the exogenous nucleic acid is stably transfected or transformed into the plant genome.

9. A method of enhancing photosynthetic efficiency and biomass yield in a plant, plant cell, or plant tissue, the method comprising expressing an exogenous nucleic acid comprising a sequence having at least 98% sequence identity to SEQ ID NO: 1 in the plant, plant cell, or plant tissue, wherein the expression of the exogenous nucleic acid comprising the sequence having at least 98% nucleotide sequence identity to SEQ ID NO: 1 results in enhanced photosynthetic efficiency and/or plant biomass of the plant, plant cell, or plant tissue as compared to a wild-type plant, plant cell or plant tissue without the genetic modification, wherein the plant is selected from *Arabidopsis* or *Populus*.

10. The method of claim 9, wherein the expression of the exogenous nucleic acid results in enhanced photosynthetic efficiency and/or plant biomass of the plant, plant cell, or plant tissue as compared to a wild-type plant, plant cell or plant tissue without the genetic modification when exposed to a stable or a fluctuating light environment.

11. The method of claim 9, wherein the nucleic acid comprising a nucleotide sequence having at least 98% sequence identity to SEQ ID NO: 1 encodes a protein comprising an amino acid sequence having at least 98% sequence identity to SEQ ID NO: 2.

12. The method of claim 11, wherein the exogenous nucleic acid is operably linked to a heterologous promoter.

13. The method of claim 12, wherein the heterologous promoter is a constitutive promoter.

14. The method of claim 12, wherein the heterologous promoter is a tissue-specific promoter.

15. The method of claim 12, wherein the heterologous promoter is a *Populus trichocarpa* native promoter.

16. The method of claim 9, wherein the exogenous nucleic acid is stably transfected or transformed into the plant genome.

* * * * *

SEQUENCE LISTING

```
Sequence total quantity: 18
SEQ ID NO: 1            moltype = DNA  length = 444
FEATURE                 Location/Qualifiers
misc_feature            1..444
                        note = PRL-1
source                  1..444
                        mol_type = other DNA
                        organism = synthetic construct
SEQUENCE: 1
atgggtcacc aaccgagact gggtcatgac agaccctatg gggttgtagg tagaaccggg  60
ttctccttcc ttcagagaac ttgtagcctc atccgcgata tttatttcac tcaagattgg  120
gtctctctac cgagtgttct gcctgtggct tcggggggta ttcacgtttg gcatatgcct  180
gctctgaccg agatctttgg agatgattcc gtactacaat tcgatggagg aactttaggg  240
cacccttggg gaattgcacc tagtgccgtt gctaatcgag tagctttaga agcatgtgta  300
caagctcgta atgagggacg tgatcttgct cgtgagggaa atgaaattat ccgtgaagct  360
agcaaatgga gccctgaact agctgctgct tgtgaagtat ggaaggagat taaatttgaa  420
ttccaagcaa tggatatgtt gtaa                                        444

SEQ ID NO: 2            moltype = AA  length = 147
FEATURE                 Location/Qualifiers
REGION                  1..147
```

```
                        note = PRL-1
source                  1..147
                        mol_type = protein
                        organism = synthetic construct
SEQUENCE: 2
MGHQPRLGHD RPYGVVGRTG FSFLQRTCSL IRDIYFTQDW VSLPSVLPVA SGGIHVWHMP  60
ALTEIFGDDS VLQFDGGTLG HPWGIAPSAV ANRVALEACV QARNEGRDLA REGNEIIREA  120
SKWSPELAAA CEVWKEIKFE FQAMDML                                      147

SEQ ID NO: 3            moltype = DNA  length = 30
FEATURE                 Location/Qualifiers
misc_feature            1..30
                        note = PRL-1 Forward Primer
source                  1..30
                        mol_type = other DNA
                        organism = synthetic construct
SEQUENCE: 3
tctatctctc tcgaccgcta tgggtcacca                                   30

SEQ ID NO: 4            moltype = DNA  length = 30
FEATURE                 Location/Qualifiers
misc_feature            1..30
                        note = PRL-1 Reverse Primer
source                  1..30
                        mol_type = other DNA
                        organism = synthetic construct
SEQUENCE: 4
gagacgtcga cgcgtaagct attcgagctc                                   30

SEQ ID NO: 5            moltype = DNA  length = 18
FEATURE                 Location/Qualifiers
misc_feature            1..18
                        note = Cas9 forward primer
source                  1..18
                        mol_type = other DNA
                        organism = synthetic construct
SEQUENCE: 5
cttacgcgtc gacgtctc                                                18

SEQ ID NO: 6            moltype = DNA  length = 22
FEATURE                 Location/Qualifiers
misc_feature            1..22
                        note = Cas9 reverse primer
source                  1..22
                        mol_type = other DNA
                        organism = synthetic construct
SEQUENCE: 6
tagcggtcga gagagataga tt                                           22

SEQ ID NO: 7            moltype = DNA  length = 21
FEATURE                 Location/Qualifiers
misc_feature            1..21
                        note = PCR primer 1F
source                  1..21
                        mol_type = other DNA
                        organism = synthetic construct
SEQUENCE: 7
ccatgtgtca ttactgcgaa a                                            21

SEQ ID NO: 8            moltype = DNA  length = 22
FEATURE                 Location/Qualifiers
misc_feature            1..22
                        note = PCR primer 1R
source                  1..22
                        mol_type = other DNA
                        organism = synthetic construct
SEQUENCE: 8
tttctcggga tttacattct cc                                           22

SEQ ID NO: 9            moltype = DNA  length = 20
FEATURE                 Location/Qualifiers
misc_feature            1..20
                        note = PCR primer 2F
source                  1..20
                        mol_type = other DNA
                        organism = synthetic construct
SEQUENCE: 9
ccgctcttat tctccgacat                                              20
```

```
SEQ ID NO: 10          moltype = DNA  length = 18
FEATURE                Location/Qualifiers
misc_feature           1..18
                       note = PCR primer 2R
source                 1..18
                       mol_type = other DNA
                       organism = synthetic construct
SEQUENCE: 10
ttacccggta cgaatcaa                                                18

SEQ ID NO: 11          moltype = DNA  length = 20
FEATURE                Location/Qualifiers
misc_feature           1..20
                       note = PCR primer 3F
source                 1..20
                       mol_type = other DNA
                       organism = synthetic construct
SEQUENCE: 11
ggagggatcg aaaccttgat                                              20

SEQ ID NO: 12          moltype = DNA  length = 20
FEATURE                Location/Qualifiers
misc_feature           1..20
                       note = PCR primer 3R
source                 1..20
                       mol_type = other DNA
                       organism = synthetic construct
SEQUENCE: 12
tctgtcatga cccagtctcg                                              20

SEQ ID NO: 13          moltype = DNA  length = 20
FEATURE                Location/Qualifiers
misc_feature           1..20
                       note = PCR primer 4F
source                 1..20
                       mol_type = other DNA
                       organism = synthetic construct
SEQUENCE: 13
actccagcta tgggtcacca                                              20

SEQ ID NO: 14          moltype = DNA  length = 20
FEATURE                Location/Qualifiers
misc_feature           1..20
                       note = PCR primer 4R
source                 1..20
                       mol_type = other DNA
                       organism = synthetic construct
SEQUENCE: 14
aggtgcgatt cacctacctg                                              20

SEQ ID NO: 15          moltype = DNA  length = 20
FEATURE                Location/Qualifiers
misc_feature           1..20
                       note = PCR primer 5F
source                 1..20
                       mol_type = other DNA
                       organism = synthetic construct
SEQUENCE: 15
agacgtggtg caacaacaac                                              20

SEQ ID NO: 16          moltype = DNA  length = 20
FEATURE                Location/Qualifiers
misc_feature           1..20
                       note = PCR primer 5R
source                 1..20
                       mol_type = other DNA
                       organism = synthetic construct
SEQUENCE: 16
aggagtcgat gcaaggtgat                                              20

SEQ ID NO: 17          moltype = DNA  length = 20
FEATURE                Location/Qualifiers
misc_feature           1..20
                       note = PCR primer 6F
source                 1..20
                       mol_type = other DNA
                       organism = synthetic construct
SEQUENCE: 17
atcaccttgc atcgactcct                                              20
```

-continued

```
SEQ ID NO: 18           moltype = DNA  length = 21
FEATURE                 Location/Qualifiers
misc_feature            1..21
                        note = PCR primer 6R
source                  1..21
                        mol_type = other DNA
                        organism = synthetic construct
SEQUENCE: 18
caacatatcc attgcttgga a                                            21
```